(12) United States Patent
Dyatkin et al.

(10) Patent No.: US 8,580,399 B2
(45) Date of Patent: Nov. 12, 2013

(54) SUBSTITUTED OLIGOAZACARBAZOLES FOR LIGHT EMITTING DIODES

(75) Inventors: Alexey Dyatkin, Ambler, PA (US); Lichang Zeng, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 121 days.

(21) Appl. No.: 13/082,914

(22) Filed: Apr. 8, 2011

(65) Prior Publication Data

US 2012/0256169 A1    Oct. 11, 2012

(51) Int. Cl.
H01L 51/54        (2006.01)

(52) U.S. Cl.
USPC ........... 428/690; 428/917; 313/504; 313/505; 313/506; 257/40; 257/E51.05; 257/E51.026; 257/E51.032; 546/18; 546/79; 546/81; 546/101; 548/440

(58) Field of Classification Search
USPC .................. 428/690, 917; 313/504, 505, 506; 257/40, E51.032, E51.05, E51.026; 546/18, 79, 81, 101; 548/440
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034856 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2005/1026044 | 11/2005 | Thompson et al. |
| 2006/0008670 A1 | 1/2006 | Lin et al. |
| 2006/0202194 A1 | 9/2006 | Jeong et al. |
| 2006/1024027 | 10/2006 | Adamovich at al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0141127 A1 | 6/2010 | Xia et al. |
| 2010/0244004 A1 | 9/2010 | Xia et al. |

FOREIGN PATENT DOCUMENTS

| | | |
|---|---|---|
| EP | 0650955 | 5/1995 |
| EP | 1725079 | 11/2006 |

(Continued)

OTHER PUBLICATIONS

The International Search Report corresponding to the PCT/US2012/032219.

Baldo et al., "Highly Efficient Phosphorescent Emission from Organic Electroluminescent Devices," Nature, vol. 395, 151-154, (1998).

(Continued)

*Primary Examiner* — Gregory Clark

(74) *Attorney, Agent, or Firm* — Duane Morris LLP

(57) ABSTRACT

Novel compounds containing substituted oligoazacarbazole chains are provided. These compounds are useful in organic light emitting devices, in particular as hosts in the emissive layer of such devices.

17 Claims, 4 Drawing Sheets

(56) References Cited

FOREIGN PATENT DOCUMENTS

| | | |
|---|---|---|
| EP | 2034538 | 3/2009 |
| EP | 2123733 | 11/2009 |
| EP | 2166583 | 3/2010 |
| EP | 2395573 | 12/2011 |
| JP | 200511610 | 1/2005 |
| JP | 2007123392 | 5/2007 |
| JP | 2007254297 | 10/2007 |
| JP | 2008074939 | 10/2009 |
| JP | 2010-135467 | * 6/2010 |
| JP | 2010135467 | 6/2010 |
| JP | 2011008991 | 1/2011 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2008056746 | 5/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | 2009085344 | 7/2009 |
| WO | WO 2009086028 | 7/2009 |
| WO | WO 2009100991 | 8/2009 |
| WO | 2010090077 | 8/2010 |

OTHER PUBLICATIONS

Baldo et al., "Very high-efficiency green organic light-emitting devices based on electrophosphorescence," Appl. Phys. Lett., vol. 75, No. 3, 4-6 (1999).

Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(/) Complex-Based Light-Emitting Diodes with Low Turn-On voltage," Appl. Phys. Lett., 74(10):1361-1363 (1999).

Gao, Zhiciiang et al., "Bright-Blue Electroluminescence From a Silyl-Substituted ter-(phenylene-vinylene) derivative," Appl. Phys. Lett., 74(6):865- 867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing N^ C^ N-Co-ordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).

Mi, Bao-Xiu et al., "Thermally Stable Hole-Transporting Material for Organic Light-Emitting Diode: an lsoindole Derivative," Chem. Mater., 15(16):3148-3151 (2003).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Niu, Yu-Hua et al., "Highly Efficient Electrophosphorescent Devices with Saturated Red Emission from a Neutral Osmium Complex," Chem. Mater., 17(13)3532-3636 (2005).

(56) References Cited

OTHER PUBLICATIONS

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto,Youichi et al., "Synthesis, Characterization, and Electron-Transport Property of Perfluorinated Phenylene Dendrimers," *J. Am. Chem. Soc.*, 122(8)1 832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko at al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

\* cited by examiner

| LiF/Al 1000 Å |
|---|
| Alq 400 Å |
| BL 50 Å |
| Compound/dopant 15% 300 Å |
| NPD 300 Å |
| HIL4 100 Å |
| ITO 800 Å |

FIGURE 4

SUBSTITUTED OLIGOAZACARBAZOLES FOR LIGHT EMITTING DIODES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention is related to host materials comprising substituted oligoazacarbazole compounds. These materials may be used in OLEDs to provide devices having improved performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

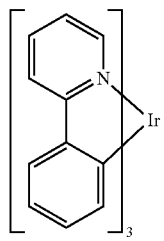

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled hi the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising substituted oligoazacarbazoles of formula I are provided,

Y—X—Z,                          Formula I.

Group Y is selected from the group consisting of:

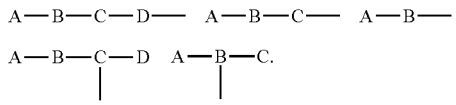

Each of A, B, C, and D are independently selected from the compound of formula II:

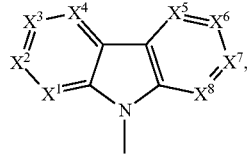

Formula II

In the compound of formula II, $X^1$ is selected from the group $C—R^1$ and N, $X^2$ is selected from the group $C—R^2$ and N, $X^3$ is selected from the group $C—R^3$ and N, $X^4$ is selected from the group $C—R^4$ and N, $X^5$ is selected from the group $C—R^5$ and N, $X^6$ is selected from the group $C—R^6$ and N, $X^7$ is selected from the group $C—R^7$ and N, and $X^8$ is selected from the group $C—R^8$ and N.

Groups A, B, C, and D are connected to each other through C—N bonds, and at least one of A, B, C, and D is not carbazole. Group X is an aryl or heteroaryl linker that is optionally further substituted, and Y and X are connected through a C—N bond.

$R_1$, $R_2$, $R_3$, $R_4$, $R_5$, $R_6$, $R_7$, and $R_8$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Group Z is selected from the group consisting of dibenzothiphene, dibenzofuran, dibenzoselenophene, aza-dibenzothiophene, aza-dibenzofuran, and aza-dibenzoselenophene that is optionally further substituted.

In one aspect, group X has the structure

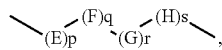

where E, F, G and H are independently selected from the group consisting of

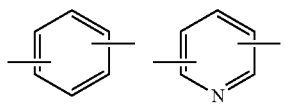

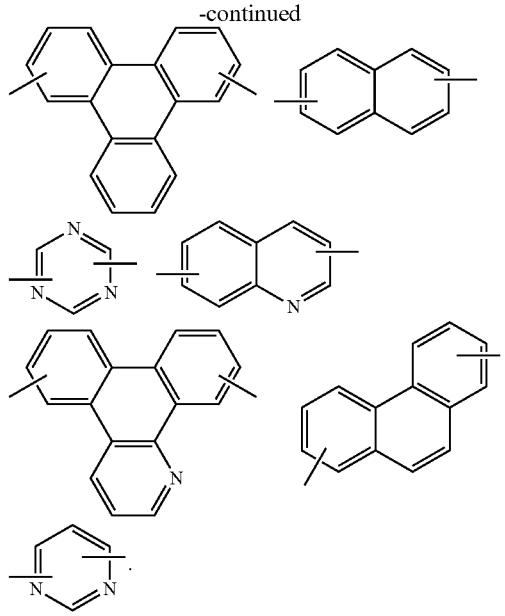

In one aspect, groups E, F, G and H are optionally further substituted with $R_9$, where $R_9$ represents mono, di, tri, or tetra substitution, and $R_9$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof. Each of p, q, r and s can have a value from 0 to 4, and p+q+r+s is at least 1.

In one aspect, the groups A, B, C, and D are connected to each other through a bond between a carbon at the 3 or 6-position and a nitrogen at the 9-position. In another aspect, Z is 2-dibenzothiophenyl, 4-dibenzothiophenyl, 2-dibenzofuranyl, or 4-dibenzofuranyl. In another aspect, A, B, C, and D are not carbazole.

In one aspect, $R_1$, $R_2$, $R_3$, $R_4$, $R_5$, $R_6$, $R_7$, and $R_9$ are independently selected from the group consisting of phenyl, biphenyl, triphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

In one aspect, A, B, C, and D are independently selected from the group consisting of:

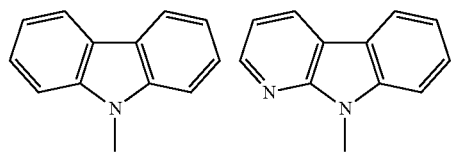

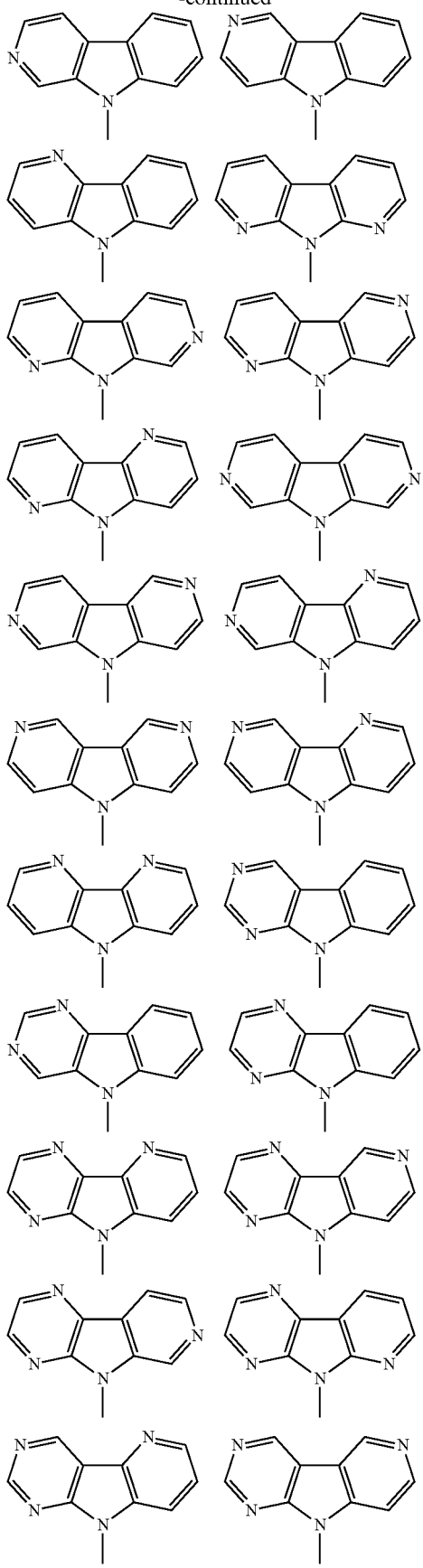

Specific non limiting examples of compounds are provided. In one aspect, the compound is selected from the group consisting of Compound 1-Compound 35.

A first device comprising an organic light emitting device is provided. The organic light emitting device further comprises an anode, a cathode, and a first organic layer disposed between the anode and the cathode. The first organic layer comprises a compound of formula I.

In one aspect, the first organic layer is an emissive layer and the compound of formula I is a host. In another aspect, the device further comprises a second organic layer that is a non-emissive layer and the compound having formula I is a material in the second organic layer. In one aspect, the organic layer further comprises an emissive compound. In one aspect, the emissive compound is a transition metal complex having at least one ligand selected from the group consisting of:

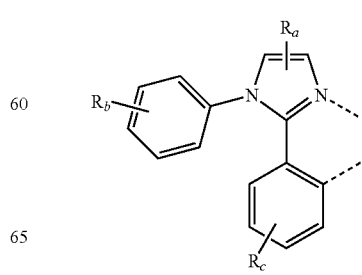

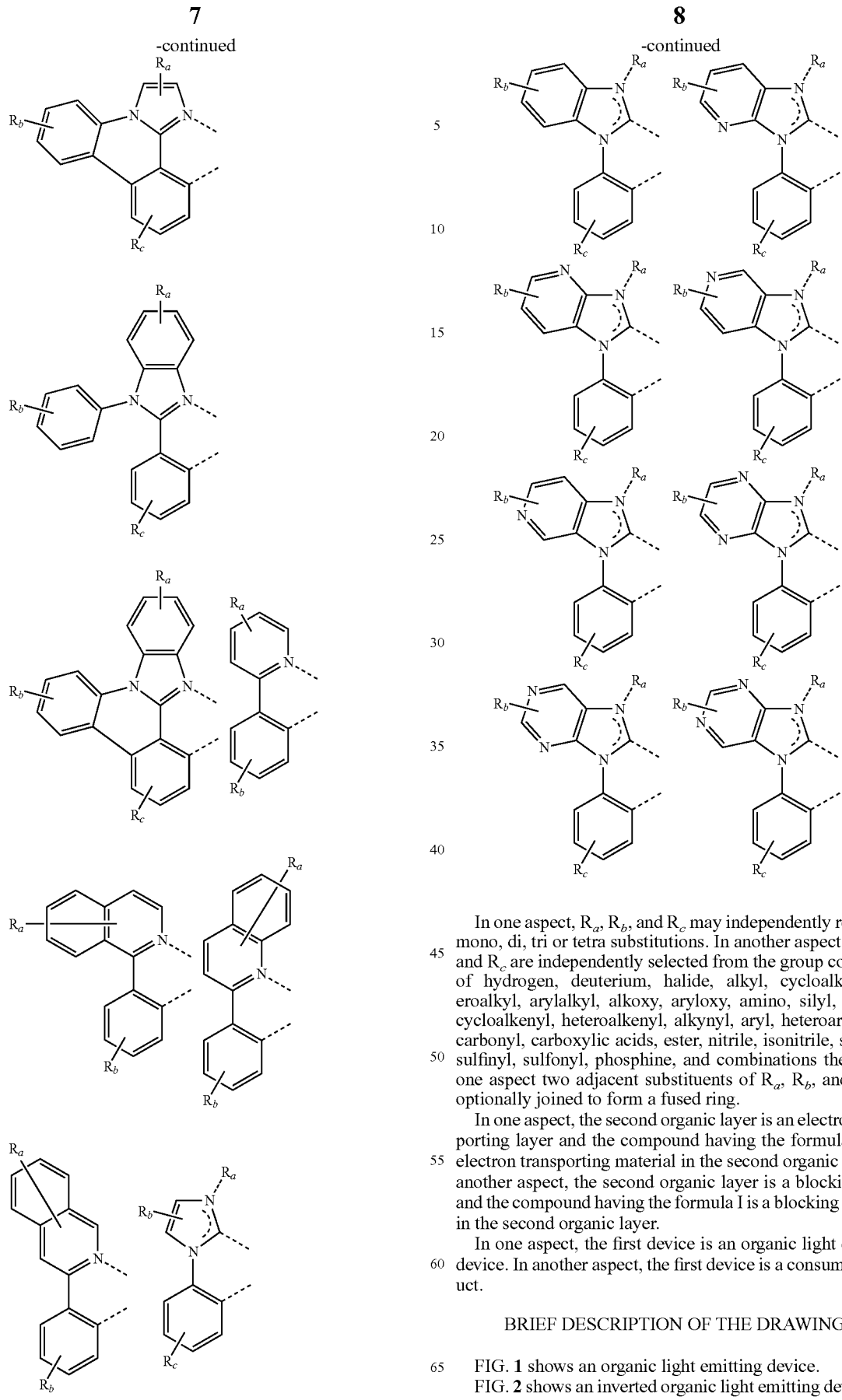

In one aspect, $R_a$, $R_b$, and $R_c$ may independently represent mono, di, tri or tetra substitutions. In another aspect, $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof. In one aspect two adjacent substituents of $R_a$, $R_b$, and $R_c$ are optionally joined to form a fused ring.

In one aspect, the second organic layer is an electron transporting layer and the compound having the formula I is an electron transporting material in the second organic layer. In another aspect, the second organic layer is a blocking layer and the compound having the formula I is a blocking material in the second organic layer.

In one aspect, the first device is an organic light emitting device. In another aspect, the first device is a consumer product.

BRIEF DESCRIPTION OF THE DRAWINGS

FIG. 4 shows an exemplary OLED structure used for testing compounds of formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
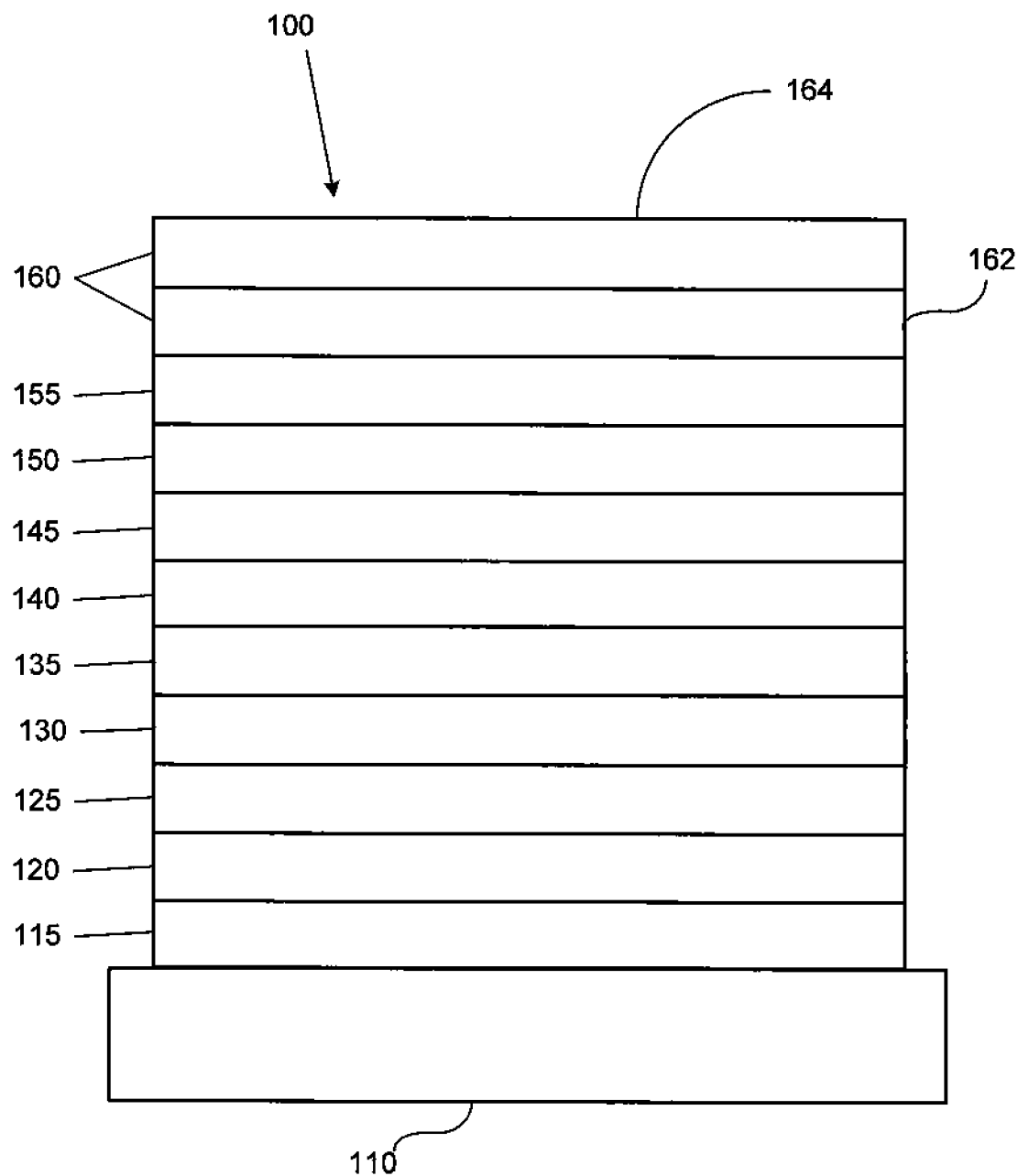
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
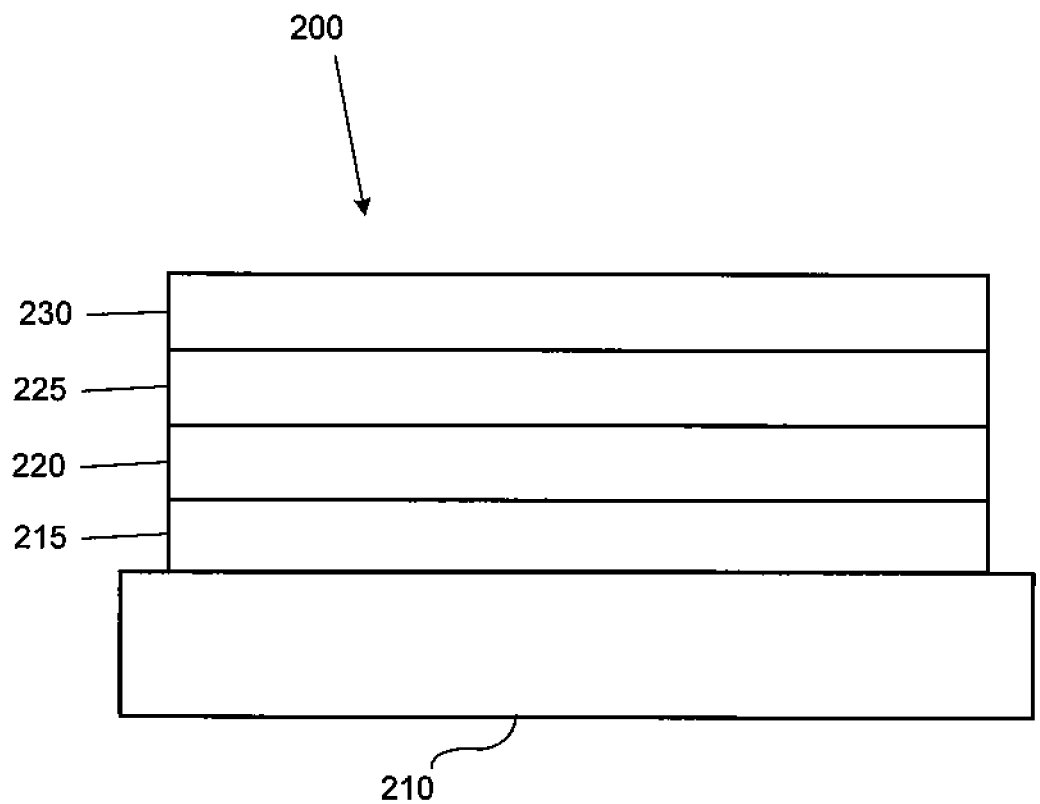
FIG. 2 shows an inverted organic light emitting device that does not have a separate electron transport layer.
Figure 3:
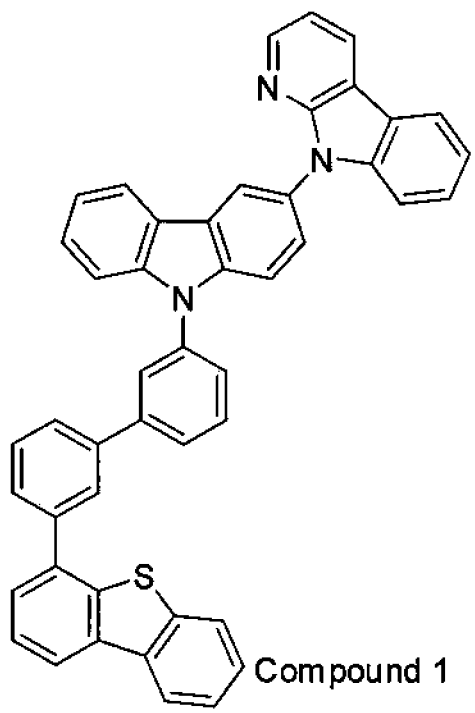
FIG. 3 shows an exemplary substituted oligoazacarbazole compound.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

The provided novel compounds consist of oligoazacarbazole and dibenzothiophene (DBT) or dibenzofuran (DBF) fragments, separated by a (poly)aromatic spacer. An "azacarbazole" is a compound of formula II wherein at least one aromatic CH group has been replaced by a nitrogen atom. An "oligoazacarbazole" consists of two or more azacarbazoles or carbazoles connected to each other.

The novel compounds presented herein have tunable properties that make them desirable for incorporation in OLED devices. The HOMO level of the compound is controlled by an oligoazacarbazole group, and the LUMO level is controlled by a DBT or DBF group. Without being bound by theory, the aromatic spacer is believed to modulate the intermolecular packing and charge transport properties of the compounds of formula I. Thus, the novel structural features of the compounds disclosed herein can allow for the simultaneous modification of HOMO and LUMO levels without interference. Additionally, these compounds can also achieve superior charge delocalization when used as, for example, host molecules in OLED devices, thereby providing better charge balance and improved device performance (i.e. efficiency, voltage and lifetime). Compounds of formula I can also be used as hole-blocking materials in OLED devices.

Without being bound by theory, introduction of one or more N atoms into a compound of formula II can improve voltage and make the resulting material a better electron carrier. An additional feature of the novel compounds disclosed herein is improved film formation properties. In particular, materials having an asymmetrical structure as a whole, may offer improved film formation. The improved film formation is believed to be a result of reduced tendency to crystallize due to the asymmetrical structure of the compounds.

Novel compounds comprising substituted oligoazacarbazoles of formula I are provided,

Formula I.

Group Y is selected from the group consisting of:

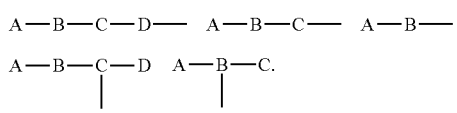

The empty valence in each of these structures represents an attachment point for group X, discussed below.

Each of A, B, C, and D are independently selected from the compound of formula II:

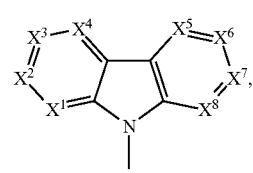
Formula II

In the compound of formula II, $X^1$ is selected from the group C—$R^1$ and N, $X^2$ is selected from the group C—$R^2$ and N, $X^3$ is selected from the group C—$R^3$ and N, $X^4$ is selected from the group C—$R^4$ and N, $X^5$ is selected from the group C—$R^5$ and N, $X^6$ is selected from the group C—$R^6$ and N, $X^7$ is selected from the group C—$R^7$ and N, and $X^8$ is selected from the group C—$R^8$ and N.

Groups A, B, C, and D are connected to each other through C—N bonds, and at least one of A, B, C, and D is not carbazole. The nitrogen in the aforementioned C—N bond is the $sp^a$ hybridized nitrogen in the compound of formula II, i.e. the nitrogen in the 9-position that is capable of having an open valence. The carbon atom in the aforementioned C—N bond is any carbon atom in the compound of formula II that is capable of forming a bond. Although "carbazole" may refer generally to compounds of formula II having the indicated substitutions, in the context of one of A, B, C, and D is not carbazole it is meant that at least one of A, B, C, and D is not a compound of formula II where $X^1$ through $X^8$ are all C—H. Group X is an aryl or heteroaryl linker that is optionally further substituted, and Y and X are connected through a C—N bond. When group X bonds through a C—N bond, the bond comprises a carbon atom capable of forming a bond on group X and the sp$^a$-hybridized nitrogen in a compound of formula II.

In one embodiment, the groups A, B, C, and D are connected to each other through a bond between a carbon at the 3 or 6-position and a nitrogen at the 9-position. In one embodiment, A, B, C, and D are not carbazole. Without being bound by theory, connecting A, B, C, and D through the 3 or 6-position is preferred because the hydrogen atom at this position is more reactive towards substitution, and by attaching A, B, C, and D through the 3 or 6-position, overall compound stability can be improved. In one embodiment, Z is 2-dibenzothiophenyl, 4-dibenzothiophenyl, 2-dibenzofuranyl, or 4-dibenzofuranyl. Connecting Z, X, A, B, C, and D as described above enables the triplet value of the compounds of formula I to be in the blue part of the spectrum.

The numbering scheme used for groups A, B, C, and D is as follows:

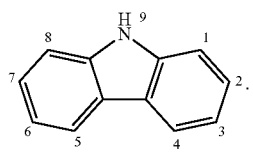

Although only carbazole is depicted, this numbering scheme applies to azacarbazoles as well.

The numbering scheme for group Z is as follows:

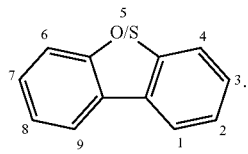

Although only dibenzothiophene/dibenzofuran is depicted, this numbering scheme applies to aza derivatives of dibenzothiophene/dibenzofuran as well.

$R_1$, $R_2$, $R_3$, $R_4$, $R_5$, $R_3$, $R_7$, and $R_8$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Group Z is selected from the group consisting of dibenzothiphene, dibenzofuran, dibenzoselenophene, aza-dibenzothiophene, aza-dibenzofuran, and aza-dibenzoselenophene that is optionally further substituted.

In one embodiment, group X has the structure

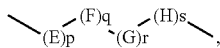

where E, F, G and H are independently selected from the group consisting of

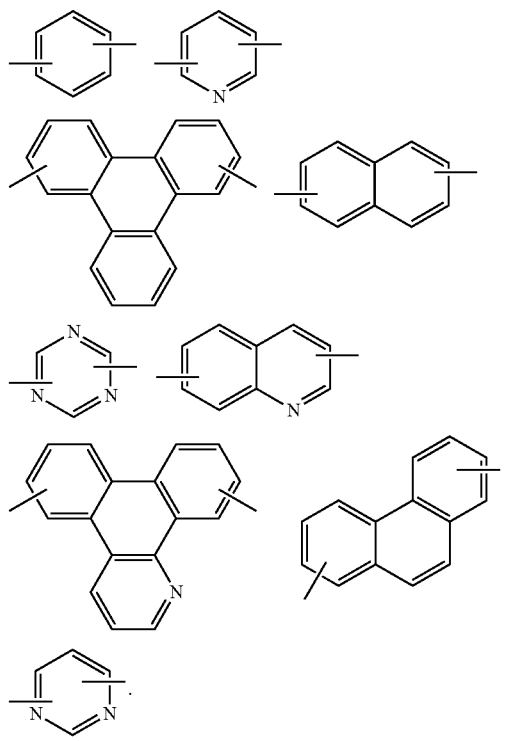

In one embodiment, groups E, F, G and H are optionally further substituted with $R_9$, where $R_9$ represents mono, di, tri, or tetra substitution, and $R_9$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof. Each of p, q, r and s can have a value from 0 to 4, and p+q+r+s is at least 1.

In one embodiment, $R_1$, $R_2$, $R_3$, $R_4$, $R_5$, $R_6$, $R_7$, and $R_8$ are independently selected from the group consisting of phenyl, biphenyl, triphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

In one embodiment, A, B, C, and D are independently selected from the group consisting of:

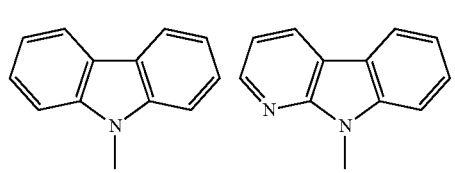

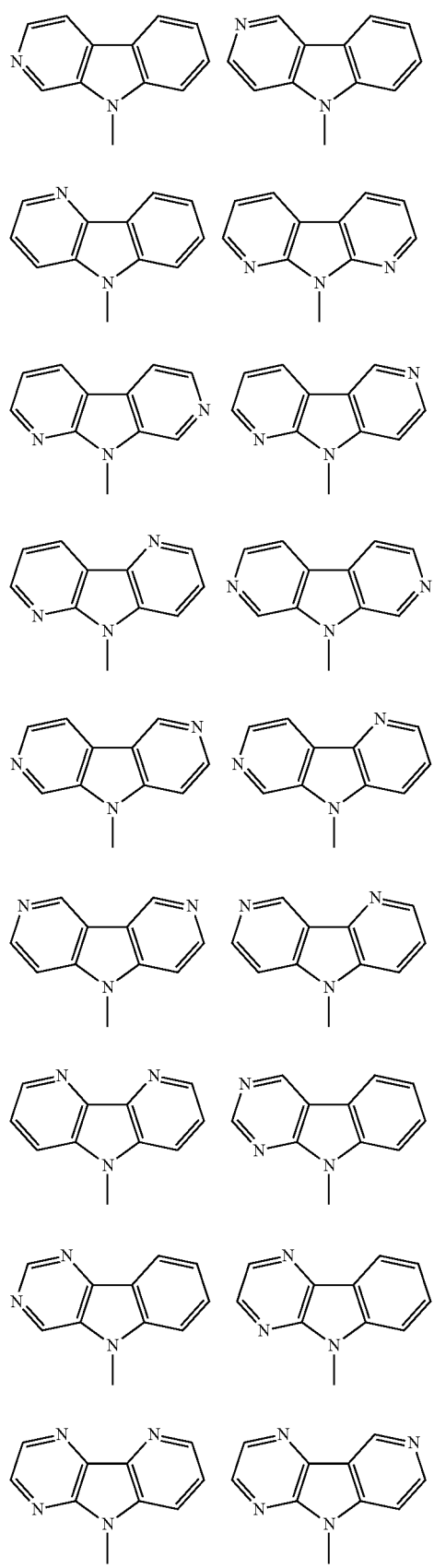
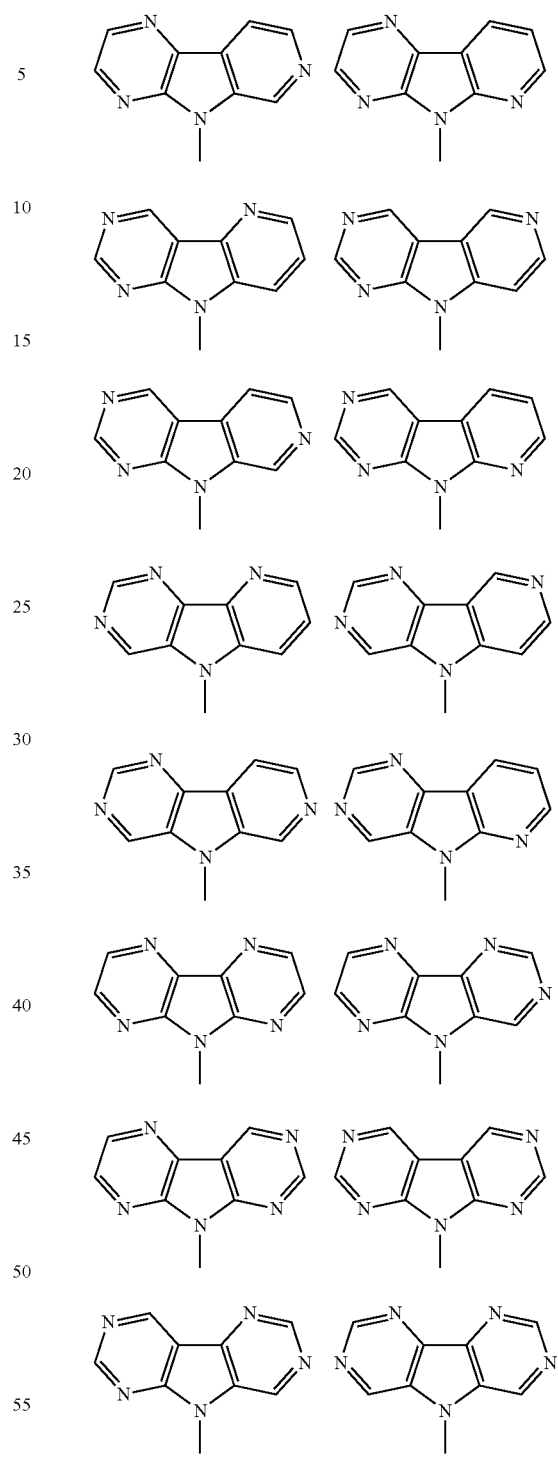

The selection of A, B, C, and D from the provided building blocks and their mutual connectivity (i.e. bonding through the C—N bond as described above) allows for the emission of light from the triplet state of these compounds to be in the blue part of the spectrum.

Specific non limiting examples of compounds are provided. In one embodiment, the compound is selected from the group consisting of Compound 1-Compound 35.

Compound 1
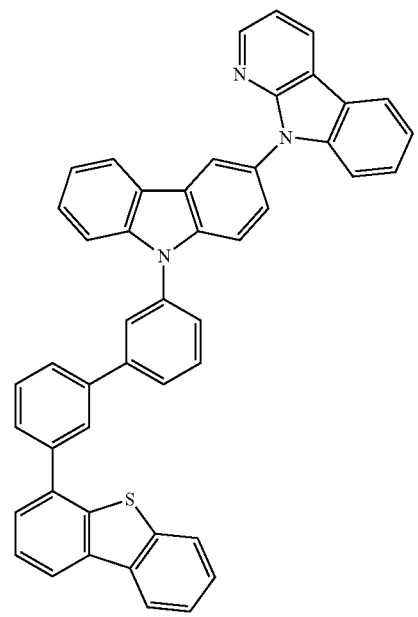
Compound 2
Compound 3
Compound 4
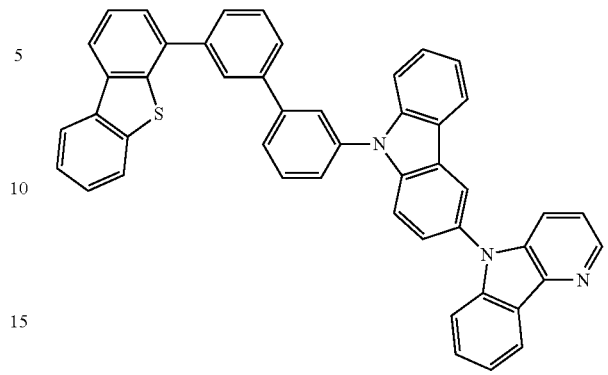
Compound 5
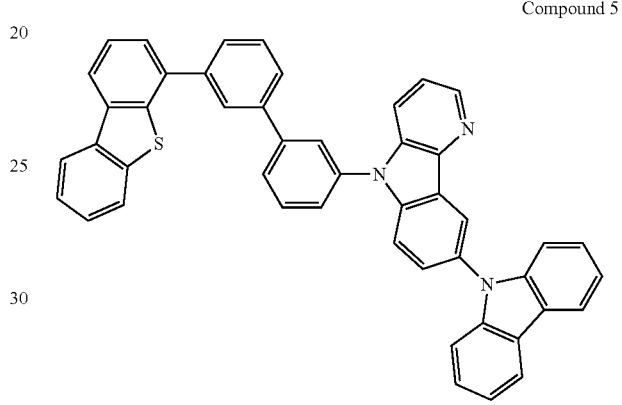
Compound 6
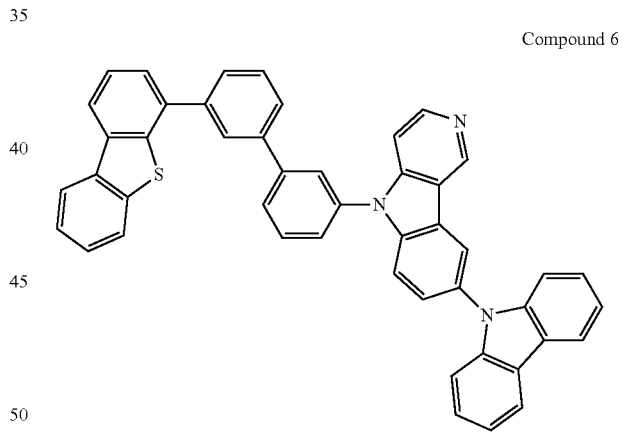
Compound 7
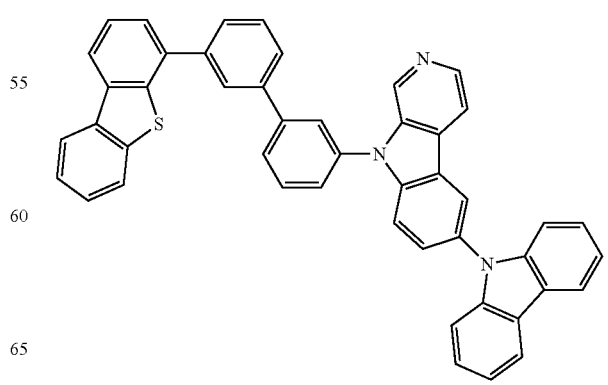

Compound 8
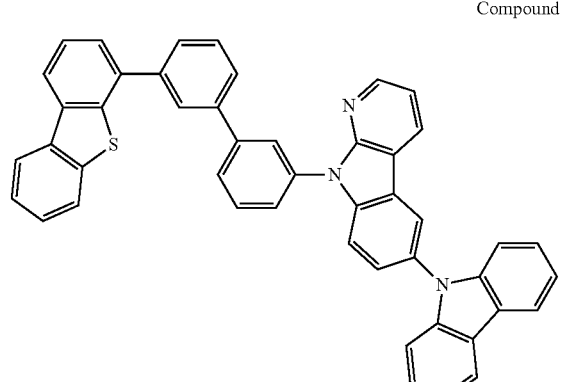
Compound 9
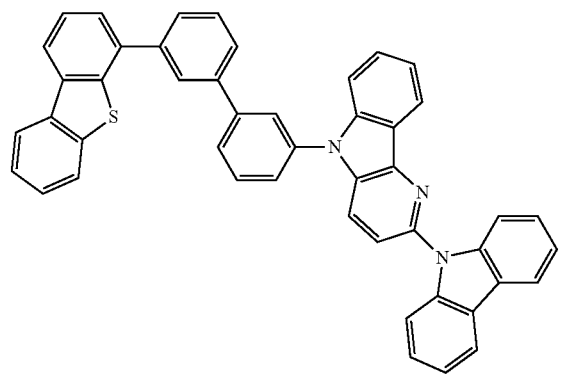
Compound 10
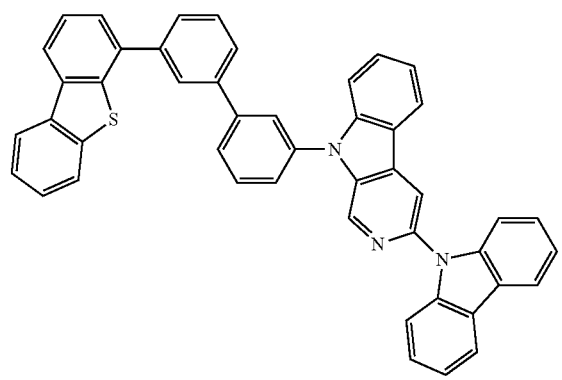
Compound 11
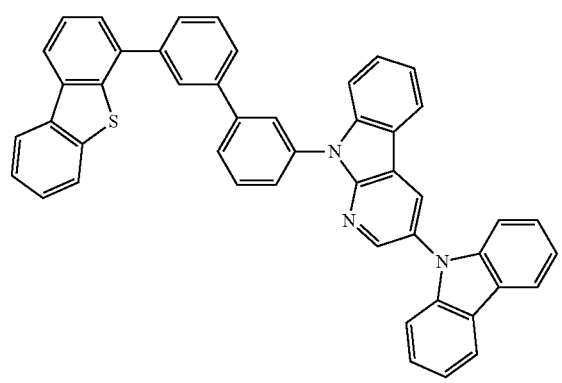
Compound 12
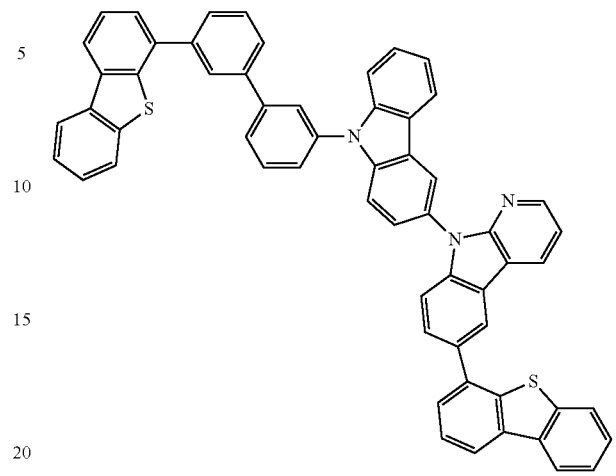
Compound 13
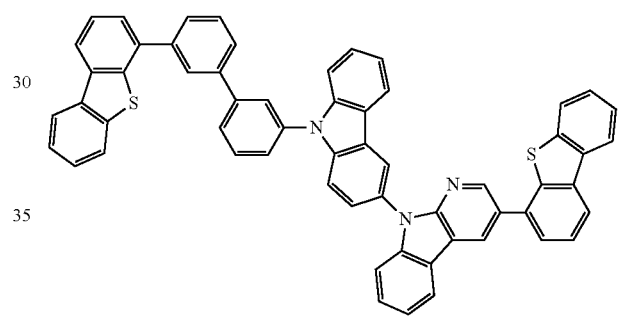
Compound 14
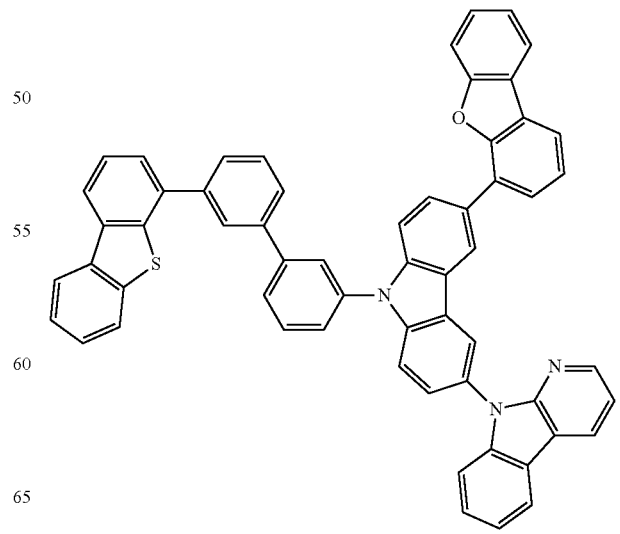

Compound 15
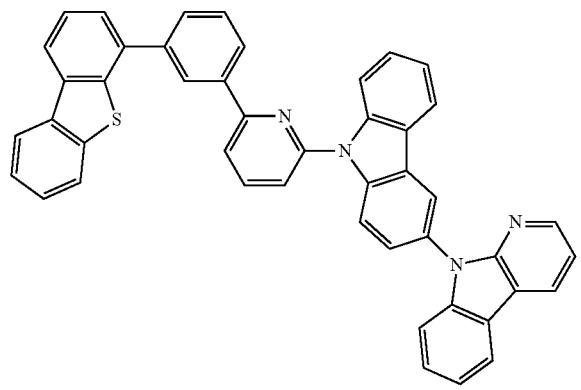
Compound 16
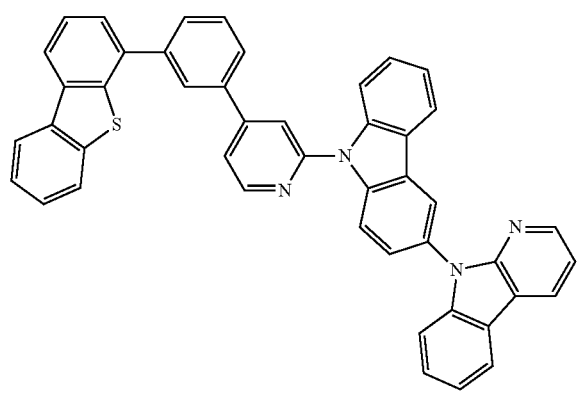
Compound 17
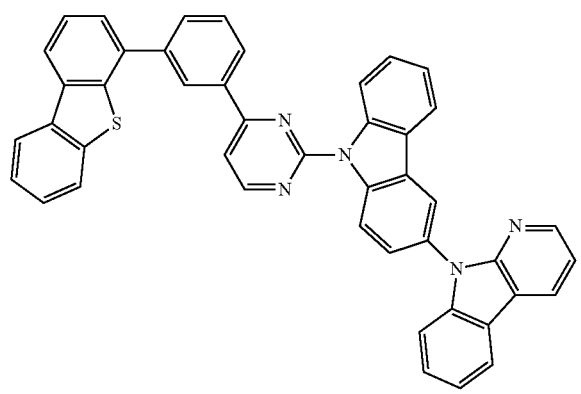
Compound 18
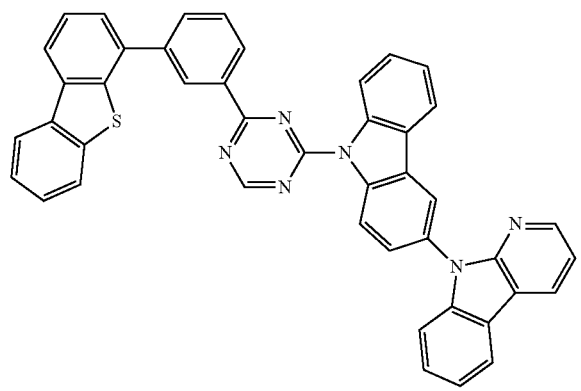
Compound 19
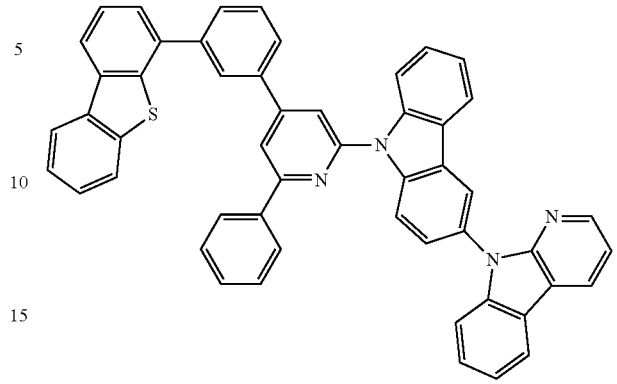
Compound 20
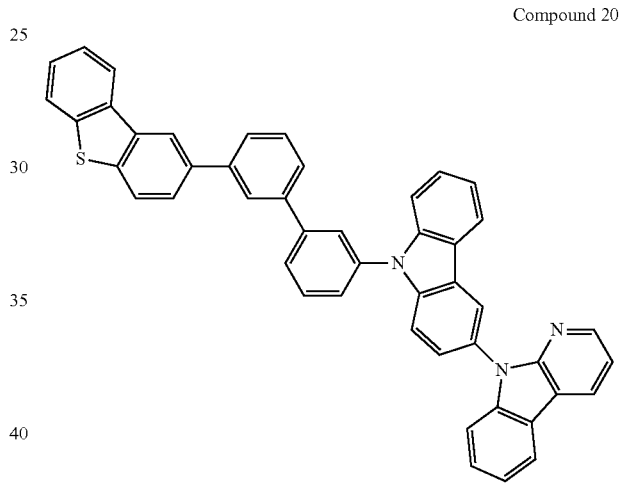
Compound 21
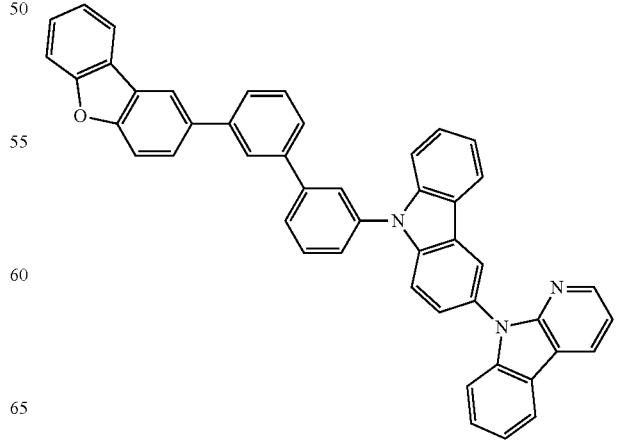

Compound 22
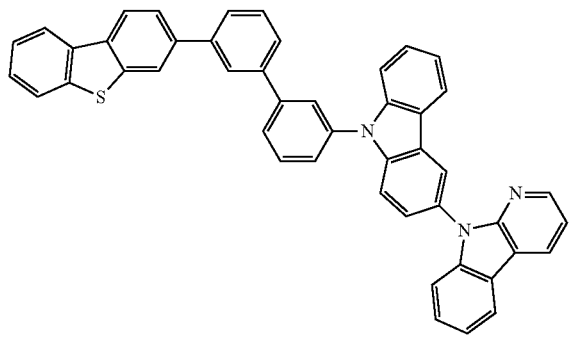
Compound 23
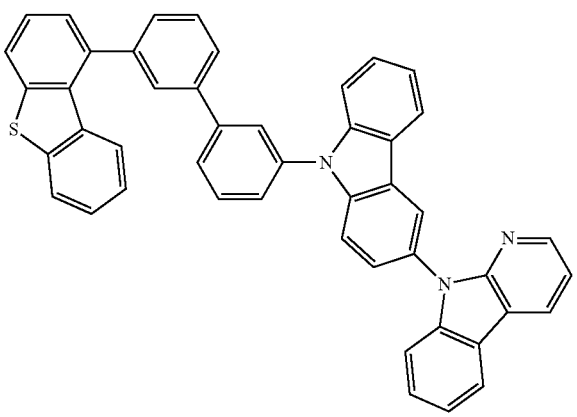
Compound 24
Compound 25
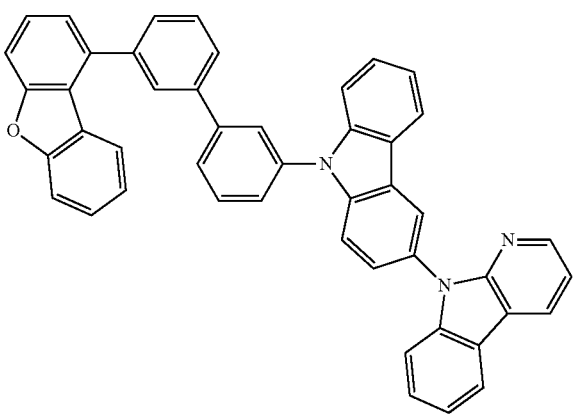
Compound 26
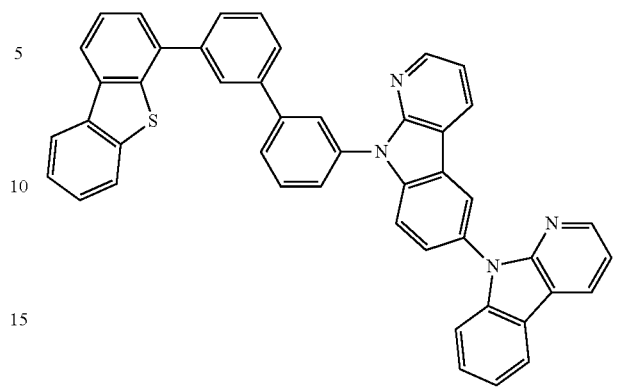
Compound 27
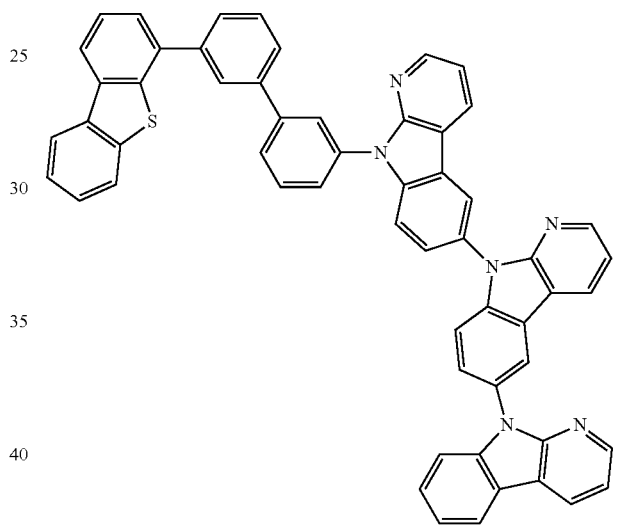
Compound 28
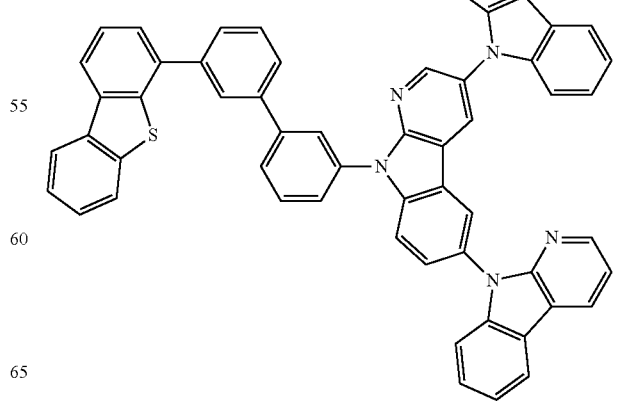

Compound 29
Compound 30
Compound 31
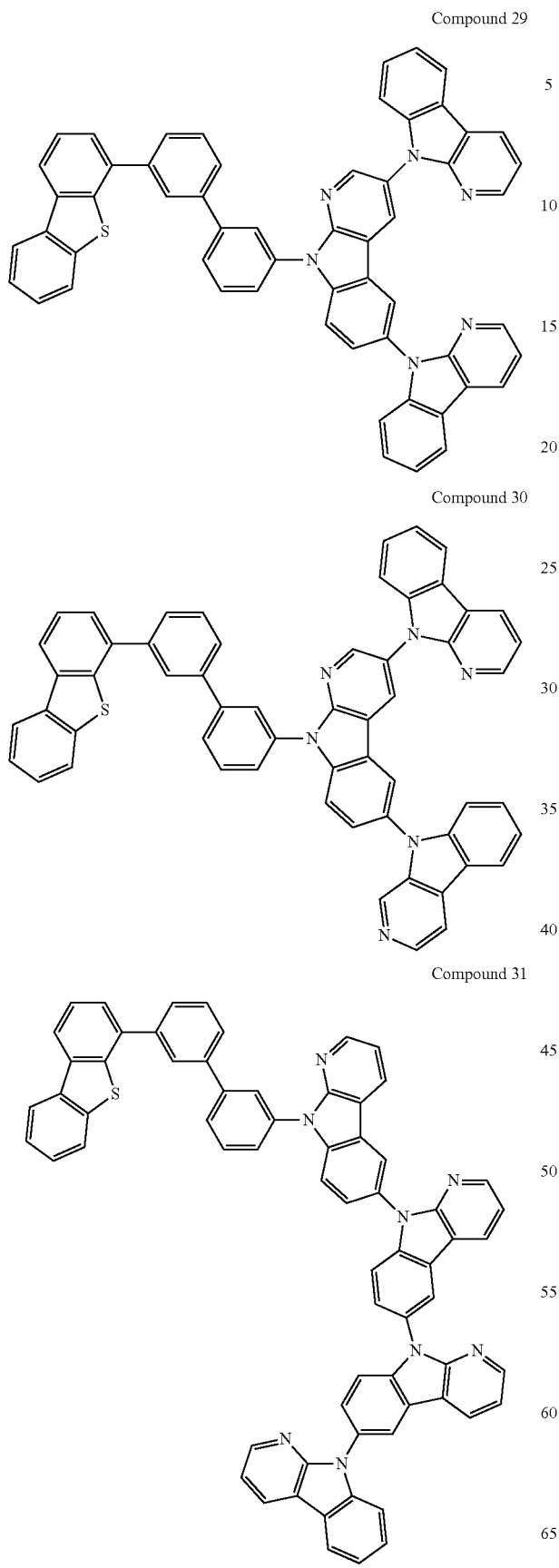
Compound 32
Compound 33
Compound 34
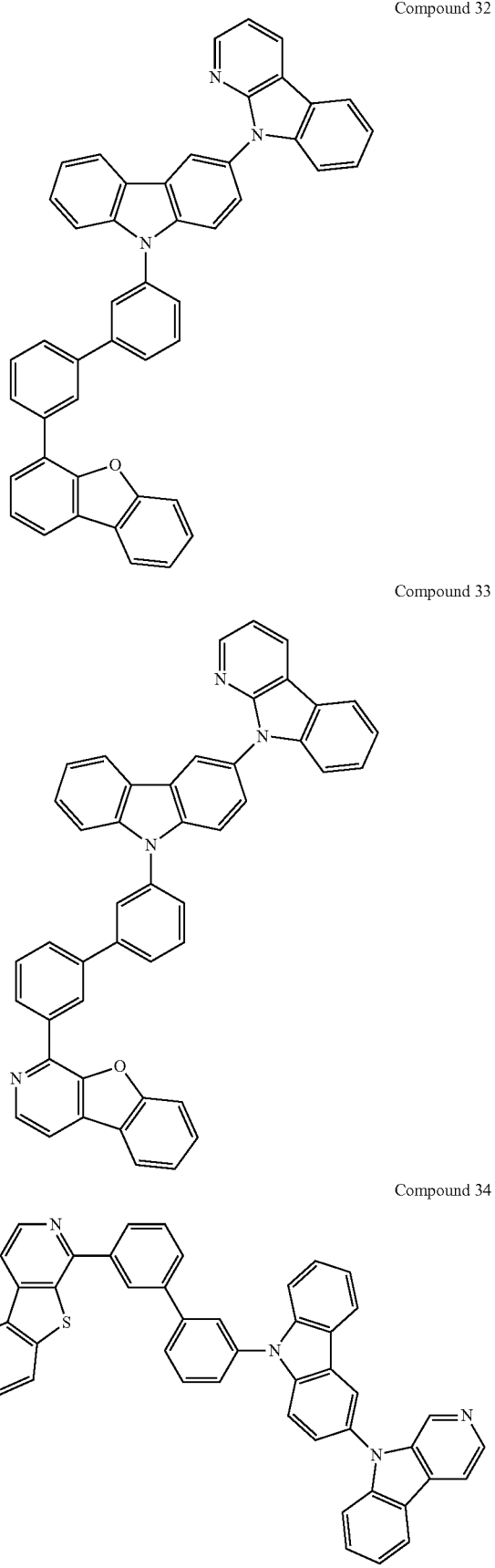

Compound 35

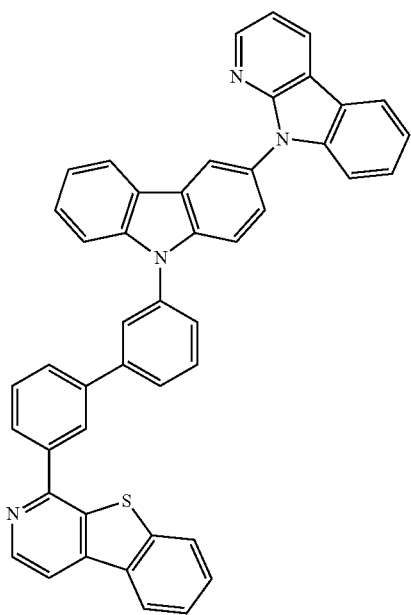

An organic light emitting device is also provided. The device can include an anode, a cathode, and a first organic layer disposed between the anode and the cathode. In one embodiment, the first organic layer comprises a compound of formula I. The organic emissive layer can include a host and a phosphorescent dopant.

In one embodiment, the first organic layer is an emissive layer and the compound of formula I is a host. In another embodiment, the device further comprises a second organic layer that is a non-emissive layer and the compound having formula I is a material in the second organic layer. In one embodiment, the organic layer further comprises an emissive compound. The emissive compound is preferably a transition metal complex having at least one ligand selected from the group consisting of:

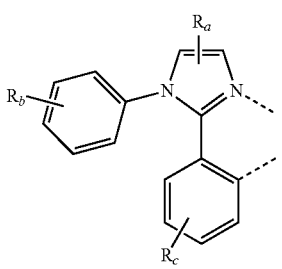

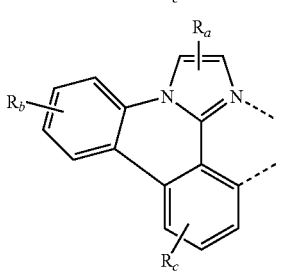

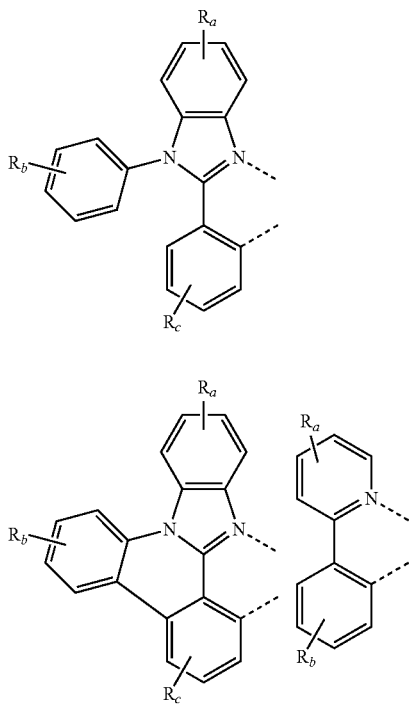

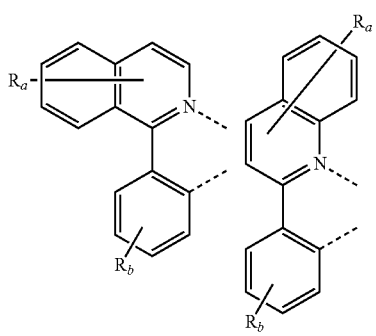

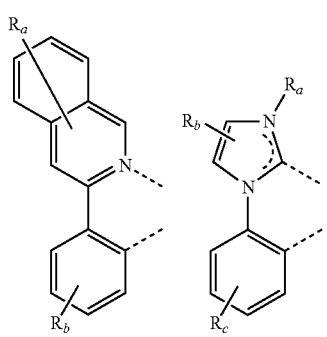

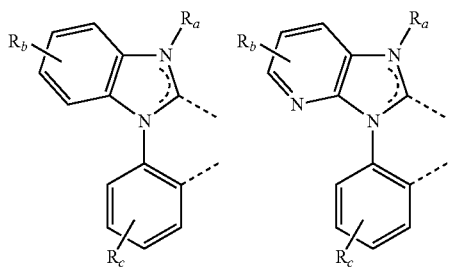

-continued

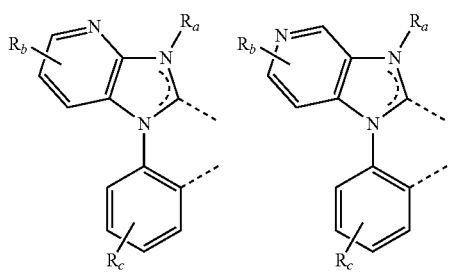
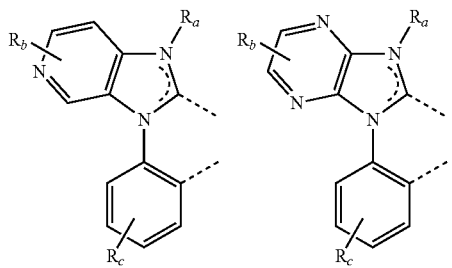
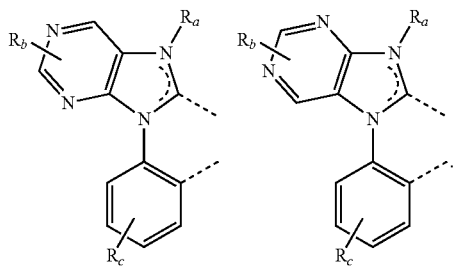

Without being bound by theory, incorporating these transition metal ligands into OLED devices enables the manufacture of OLED devices with highly desirable properties, e.g. high efficiency, long triplet lifetimes, etc.

In one embodiment, $R_a$, $R_b$, and $R_c$ independently represent mono, di, tri or tetra substitutions. In another embodiment, $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof. In one embodiment two adjacent substituents of $R_a$, $R_b$, and $R_c$ are optionally joined to form a fused ring.

In one embodiment, the second organic layer is an electron transporting layer and the compound having the formula I is an electron transporting material in the second organic layer. In another embodiment, the second organic layer is a blocking layer and the compound having the formula I is a blocking material in the second organic layer. As described below, the use of compounds of formula I in OLED devices is advantageous because of their desirable properties, e.g. quantum efficiency, luminance, etc.

An exemplary OLED device incorporating the novel compounds described herein as well as comparative compounds is depicted in FIG. 4. The OLED device was made with vacuum thermal deposition techniques known to those of skill in the art.

The components of the OLED device in FIG. 4 are as follows: 800 Å of ITO surface electrode, 100 Å of Compound HIL as the hole injection layer, 300 Å of Compound NPD as the hole transporting layer (HTL), 300 Å of Compound 1 (Cmpd. 1) or Comparison Compound (Comp. Cmpd.) doped with 15 wt % of Dopant Compound as the emissive layer (EML), 50 Å of Compound 1 or Compound BL as the blocking layer, and 400 Å of Alq$_3$ as the ETL.

The structures of the OLED layer components are as follows:

Dopant Compound

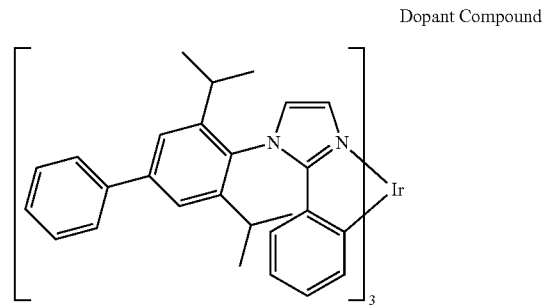

Compound BL

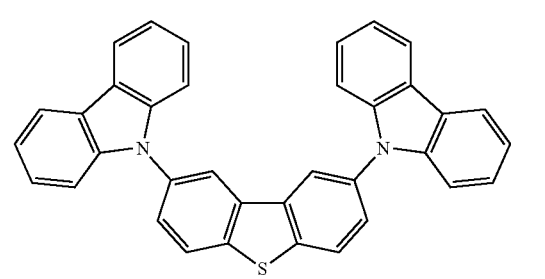

Compound HIL

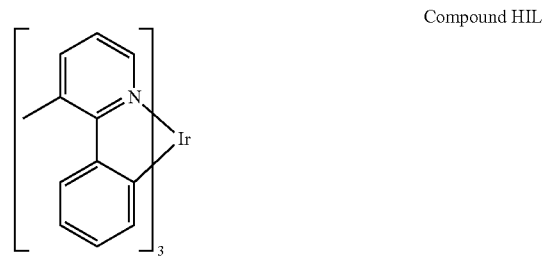

Alq

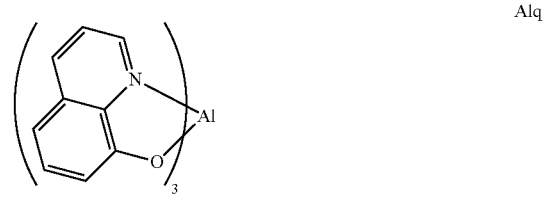

Compound NPD

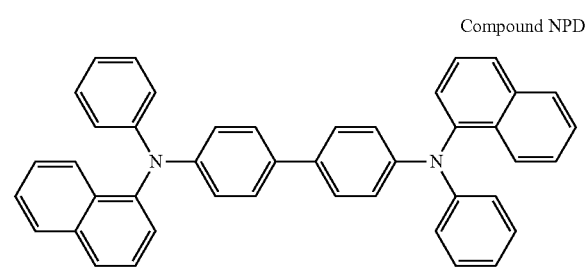

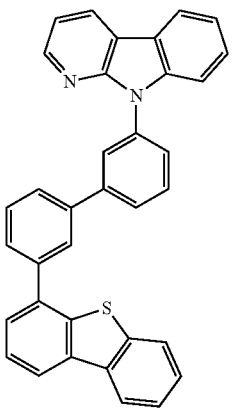

Comparison Compound

Table 1 lists the results obtained using novel Compound 1 compared to Comparison Compound in an OLED device.

TABLE 1

| Example | Host | Blocking Layer | 1931 CIE x | 1931 CIE y | $\lambda_{max}$ (nm) | At 1000 cd/m² Voltage (V) | LE (cd/A) | EQE (%) | PE (lm/W) | LT at 20 mA/cm² LT80 (h) |
|---|---|---|---|---|---|---|---|---|---|---|
| Device Example 1 | Cmpd 1 | Cmpd. BL | 0.184 | 0.405 | 474 | 7.5 | 39.4 | 16.9 | 16.5 | 58 |
| Device Comp. Example 1 | Comp. Cmpd | Cmpd. BL | 0.182 | 0.410 | 474 | 6.9 | 34.9 | 14.9 | 16.0 | 38 |
| Device Example 2 | Cmpd 1 | Cmpd. 1 | 0.184 | 0.405 | 474 | 8 | 39.4 | 16.9 | 15.4 | 52 |
| Device Comp. Example 2 | Comp. Cmpd | Comp. Cmpd. | 0.182 | 0.409 | 474 | 7.6 | 33.1 | 14.2 | 13.6 | 32 |

The OLED device in Example 1 and Comparative Example 1 in Table 1 have the same structure except in the first case Compound 1 was used as the host, while in the second case Comparison Compound was used as the host. In both cases Compound BL was used as a blocking layer. It is readily apparent from Table 1, that Compound 1 provided better luminance efficiency (LE), external quantum efficiency (EQE), and power efficiency (PE) and significantly better device lifetime than the Comparison Compound. $LT_{80}$ is defined as the time required for the initial luminance, $L_0$, to drop from 100% to 80% under constant current density at room temperature. Similar results were observed when Compound 1 and the Comparison Compound were used in the blocking layer instead of as hosts. In all cases, the use of Compound 1 provided devices with greater efficiencies and lifetimes than the Comparison Compound.

The data suggests that use of compounds of formula I, which contain an oligoazacarbazole and dibenzothiophene or dibenzofuran moieties linked by an aromatic spacer, as the blocking layer or the host, result in higher device stability compared to compounds with a single azacarbazole moiety and dibenzothiophene moiety (i.e. the Comparison Compound). Oligoazacarbazole, the main HOMO contributor in compounds of formula I, is more electron rich than azacarbazole. Compounds of formula I, such as Compound I, are superior to compounds similar to the Comparison Compound because the higher HOMO level of compounds of formula I can increase hole injection from the HTL and hole transport in the EML. These properties of compounds of formula I can result in better device charge balance and/or location of charge recombination, leading to improved device lifetime.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed below. The list includes non-limiting classes of materials, non-limiting examples of compounds for each class, and references that disclose the materials.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

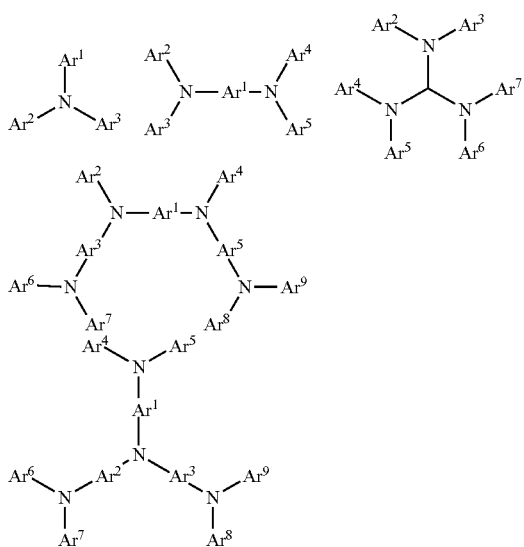

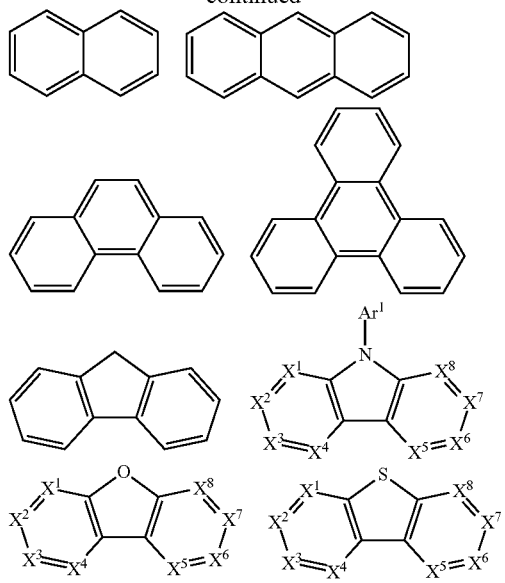

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

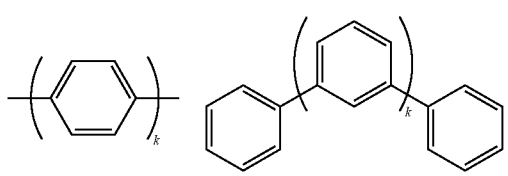

k is an integer from 1 to 20; $X^1$ to $X^8$ is CH or N; $Ar^1$ has the same group defined above.

Examples of metal complexes used in HIL or HTL include, but not limit to the following general formula:

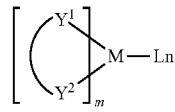

M is a metal, having an atomic weight greater than 40; $(Y^1-Y^2)$ is a bindentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic. EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

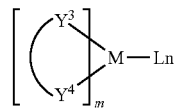

M is a metal; $(Y^3-Y^4)$ is a bindentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

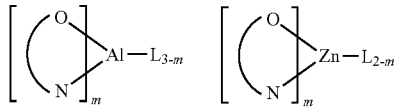

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, tiphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

In one aspect, host compound contains at least one of the following groups in the molecule:

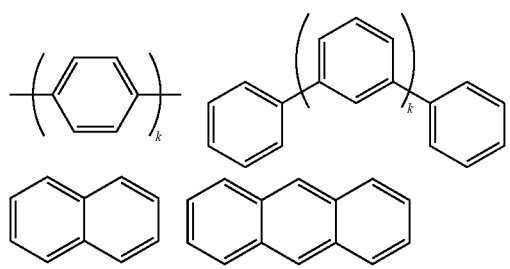

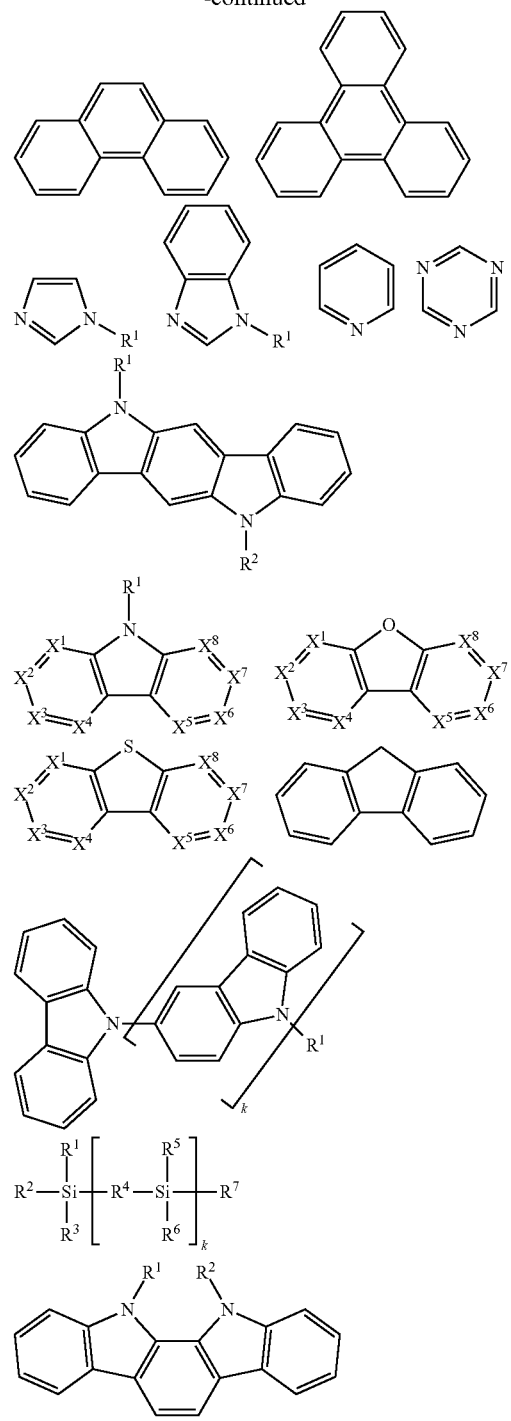

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

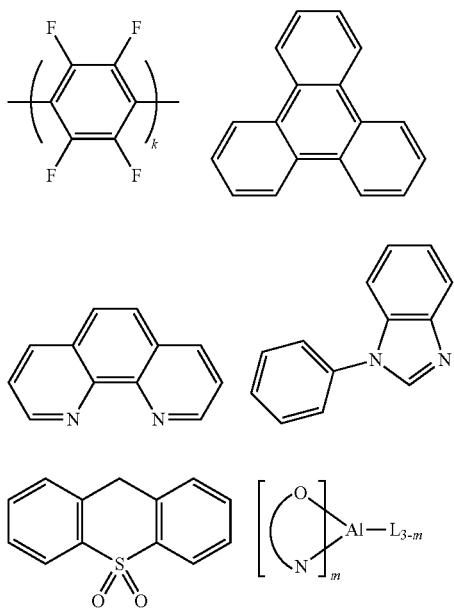

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

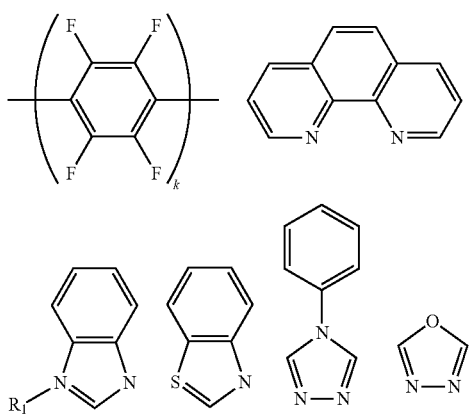

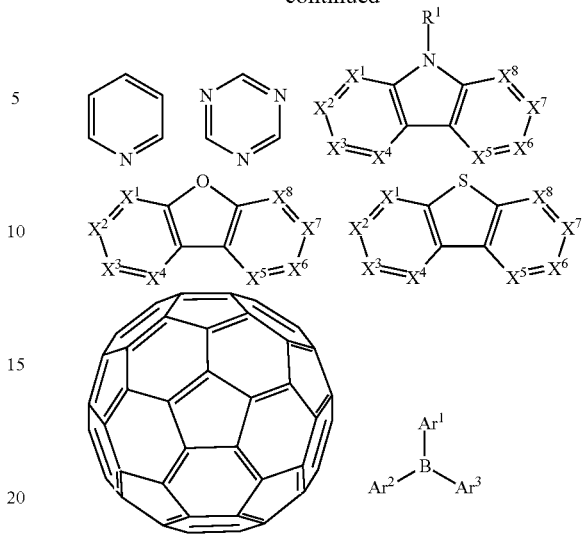

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof, when it is aryl or heteroaryl, it has the similar definition as Al's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in ETL contains, but not limit to the following general formula:

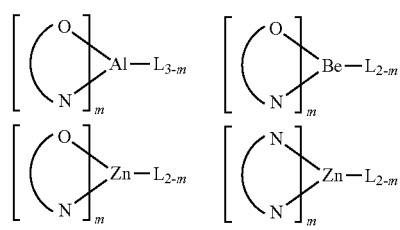

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATION |
|---|---|---|
| *Hole injection materials* | | |
| phthalocyanine and porphryin compounds | (Cu phthalocyanine structure) | Appl. Phys. Lett. 69, 2160 (1996) |
| Starburst triarylamines | (starburst triarylamine structure) | J. Lumin. 72-74, 985 (1997) |
| CF$_x$ Fluorohydrocarbon polymer | $-[CH_xF_y]_n-$ | Appl. Phys. Lett. 78, 673 (2001) |
| Conducting polymers (e.g., PEDOT:PSS, polyamline, polypthiophene) | (PEDOT:PSS structure) | Synth. Met. 87, 171 (1997) WO2007002683 |
| Phosphonic acid and sliane SAMs | (N(C$_6$H$_4$SiCl$_3$)$_3$ structure) | US20030162053 |

TABLE 2-continued
| MATERIAL | EXAMPLES OF MATERIAL | PUBLICATION |
|---|---|---|
| Triarylamine or polythiophene polymers with conductivity dopants | 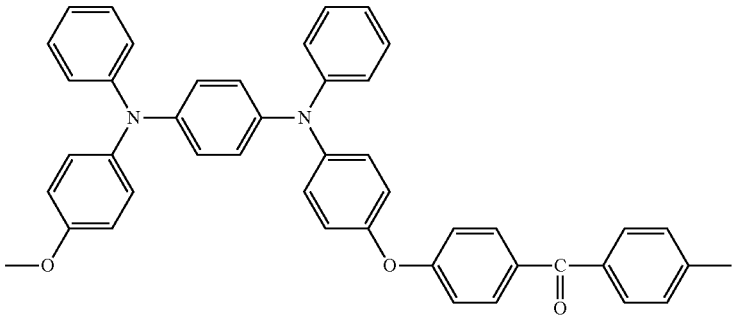 and 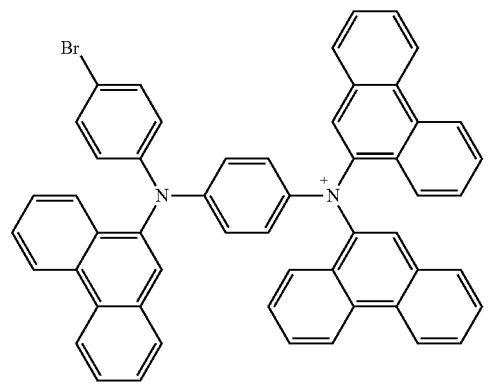 [SMILES: Brc1ccc(N(c2ccc(N(c3cc4ccccc4c4ccccc34)c3cc4ccccc4c4ccccc34)cc2)c2cc3ccccc3c3ccccc23)cc1] 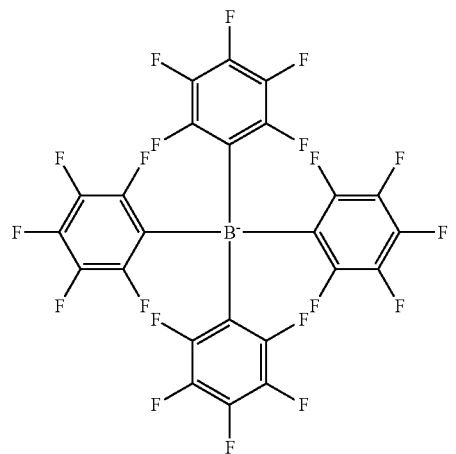 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Arylamines complexed with metal oxides such as molybdenum and tungsten oxides | 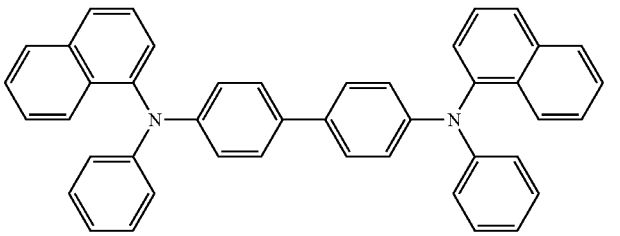 + MoO$_x$ | SID Symposium Digest, 37, 923 (2006) WO2009018009 |

TABLE 2-continued
| MATERIAL | EXAMPLES OF MATERIAL | PUBLICATION |
|---|---|---|
| p-type semiconducting organic complexes | 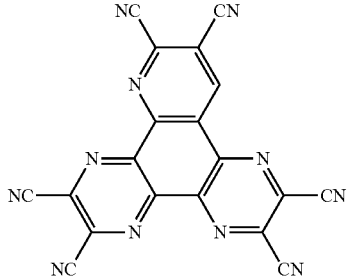 [SMILES: N#Cc1cc2c(nc1C#N)c1nc(C#N)c(C#N)nc1c1nc(C#N)c(C#N)nc21] | US20020158242 |
| Metal organometallic complexes | 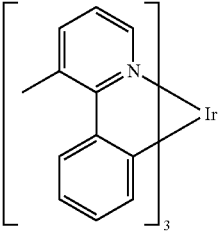 | US20060240279 |
| Cross-linkable compounds | 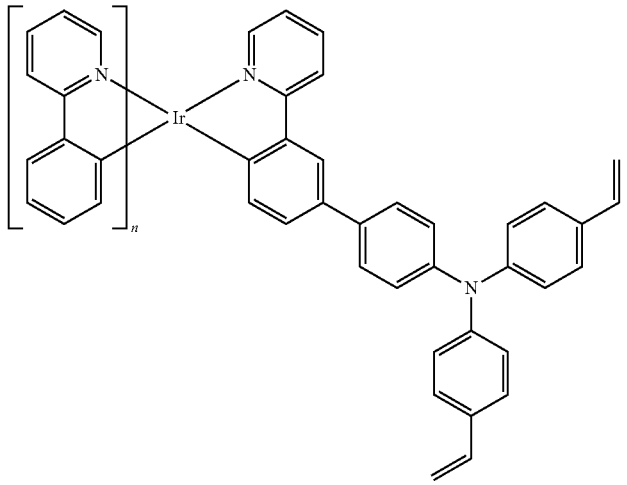 | US20080220265 |
| Hole transporting materials | | |
| Triarylamines (e.g., TPD, α-NPD) | 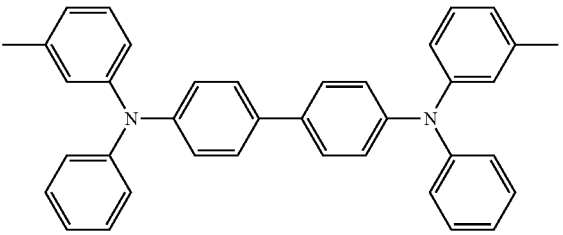 | Appl. Phys. Lett. 51, 913 (1987) |
| | 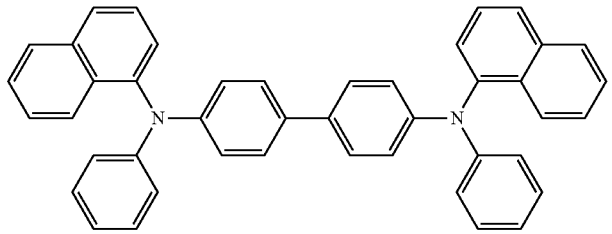 [SMILES: c1ccc(N(c2ccc(-c3ccc(N(c4ccccc4)c4cccc5ccccc45)cc3)cc2)c2cccc3ccccc23)cc1] | US5061569 |

TABLE 2-continued
| MATERIAL | EXAMPLES OF MATERIAL | PUBLICATION |
|---|---|---|
| | 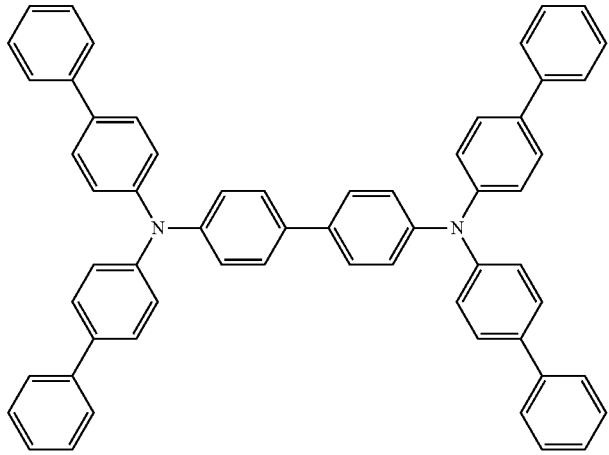 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 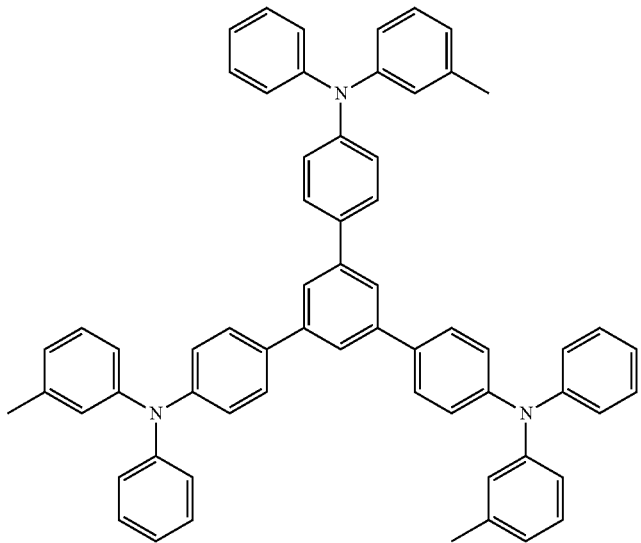 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 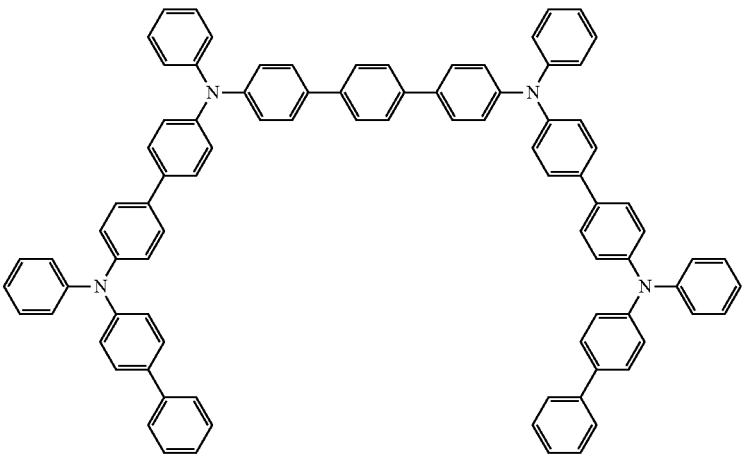 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 2-continued

| MATERIAL | EXAMPLES OF MATERIAL | PUBLICATION |
|---|---|---|
|  |  | Appl. Phys. Lett. 90, 183503 (2007) |
| Triaylamine on spirofluorene core |  | Synth. Met. 91, 209 (1997) |
| Arylamine carbazole compounds |  | Adv. Mater. 6, 677 (1994), US20080124572 |
| Triarylamine with (di)benzothiophene/ (di)benzofuran |  | US20070278938, US20080106190 |

TABLE 2-continued

| MATERIAL | EXAMPLES OF MATERIAL | PUBLICATION |
|---|---|---|
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials

Red hosts

| | | |
|---|---|---|
| Arylcarbazoles | | Appl. Phys. Lett. 78, 1622 (2001) |

TABLE 2-continued
| MATERIAL | EXAMPLES OF MATERIAL | PUBLICATION |
|---|---|---|
| Metal 8-hydroxyquinolates (e.g., Alq$_3$, BAlq) | 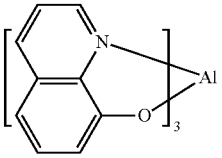 | Nature 395, 151 (1998) |
| | 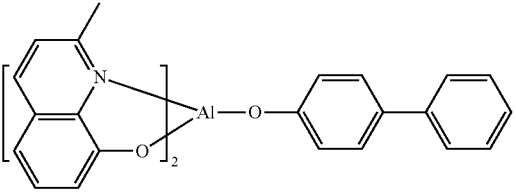 | US20060202194 |
| | 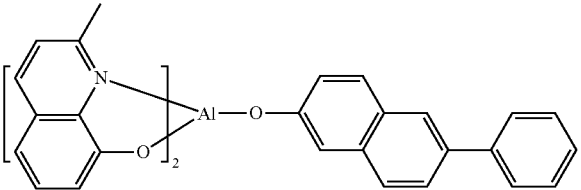 | WO2005014551 |
| | 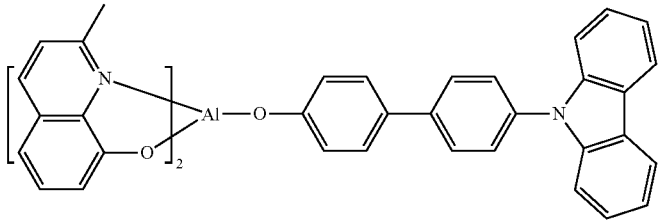 | WO2006072002 |
| Metal phenoxybenzothiazole compounds | 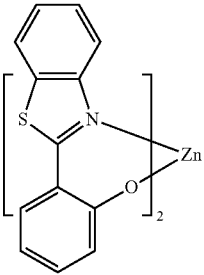 | Appl. Phys. Lett. 90, 123509 (2007) |
| Conjugated oligomers and polymers (e.g., polyfluorene) | 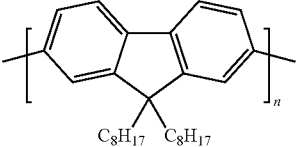 | Org. Electron. 1, 15 (2000) |
| Aromatic fused rings | 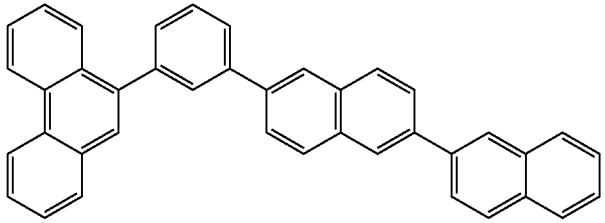 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 2-continued
| MATERIAL | EXAMPLES OF MATERIAL | PUBLICATION |
| --- | --- | --- |
| Zinc complexes | 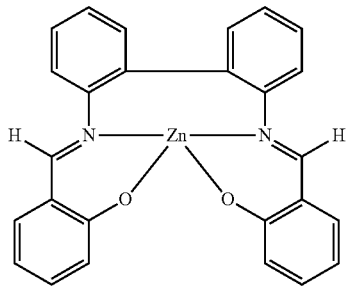 | WO2009062578 |
| Green hosts | | |
| Arylcarbazoles | 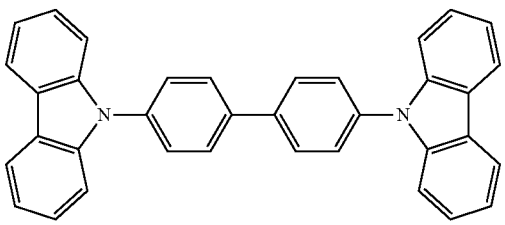 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 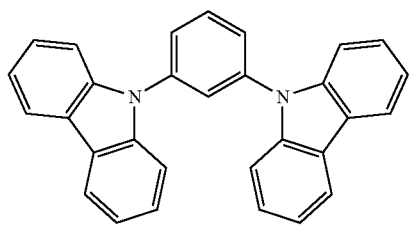 [SMILES: c1cc(-n2c3ccccc3c3ccccc32)cc(-n2c3ccccc3c3ccccc32)c1] | US20030175553 |
| | 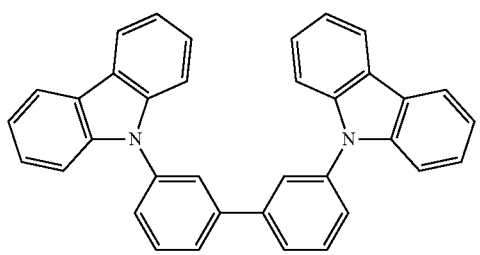 [SMILES: c1cc(-c2cccc(-n3c4ccccc4c4ccccc43)c2)cc(-n2c3ccccc3c3ccccc32)c1] | WO2001039234 |
| Aryltriphenylene compounds | 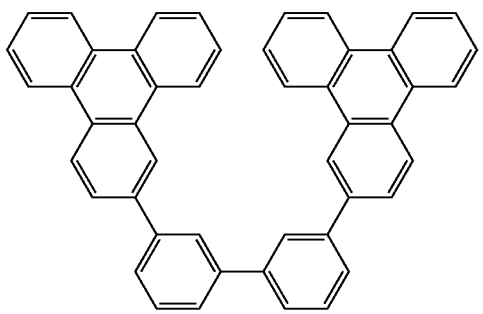 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 2-continued
| MATERIAL | EXAMPLES OF MATERIAL | PUBLICATION |
|---|---|---|
| | 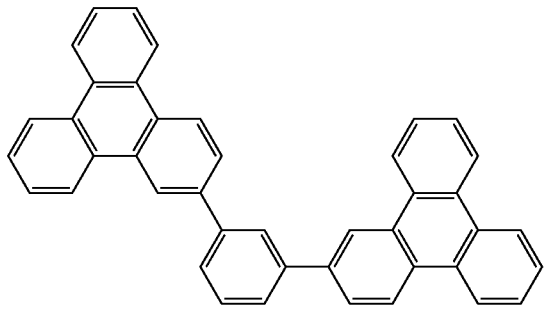 [SMILES: c1cc(-c2ccc3c4ccccc4c4ccccc4c3c2)cc(-c2ccc3c4ccccc4c4ccccc4c3c2)c1] | US20060280965 |
| | 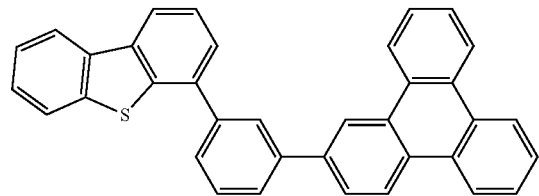 [SMILES: c1cc(-c2ccc3c4ccccc4c4ccccc4c3c2)cc(-c2cccc3c2sc2ccccc23)c1] | WO2009021126 |
| Donor acceptor type molecules | 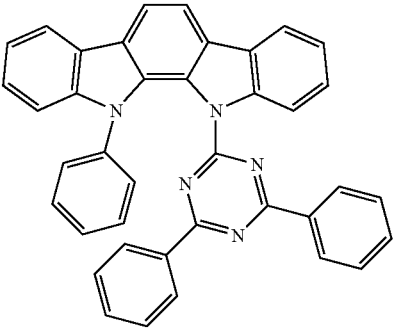 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/ DBT/DBF | 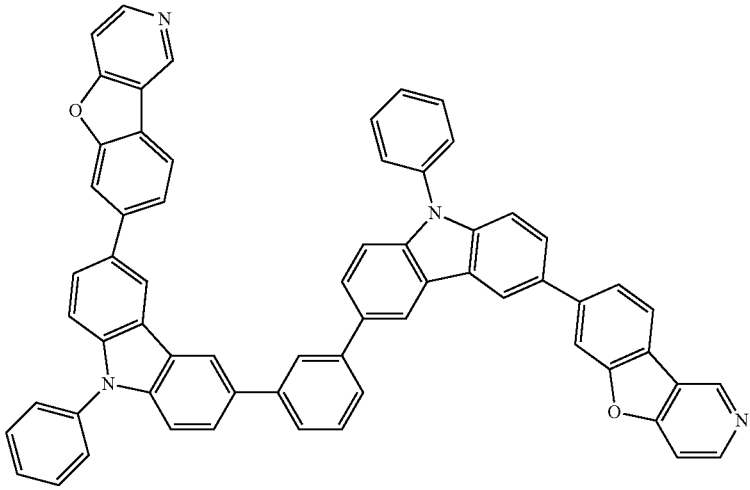 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 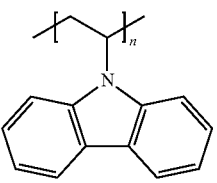 | Appl. Phys. Lett. 77, 2280 (2000) |

TABLE 2-continued

| MATERIAL | EXAMPLES OF MATERIAL | PUBLICATION |
|---|---|---|
| Spirofluorene compounds | | WO2004093207 |
| Metal phenoxybenzoxazole compounds | | WO2005089025 |
| | | WO2006132173 |
| | | JP200511610 |
| Spirofluorene-carbazole compounds | | JP2007254297 |

TABLE 2-continued

| MATERIAL | EXAMPLES OF MATERIAL | PUBLICATION |
|---|---|---|
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |

TABLE 2-continued

| MATERIAL | EXAMPLES OF MATERIAL | PUBLICATION |
| --- | --- | --- |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |

TABLE 2-continued
| MATERIAL | EXAMPLES OF MATERIAL | PUBLICATION |
|---|---|---|
| Dibenzothiophene/ Dibenzofuran- carbazole compounds | 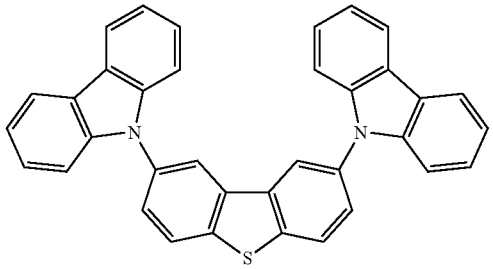 [SMILES: c1ccc2c(c1)c1ccccc1n2-c1ccc2sc3ccc(-n4c5ccccc5c5ccccc54)cc3c2c1] | WO2006114966, US20090167162 |
| | 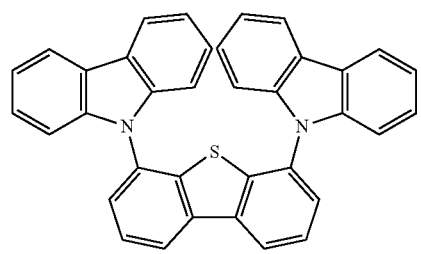 [SMILES: c1cc(-n2c3ccccc3c3ccccc32)c2sc3c(-n4c5ccccc5c5ccccc54)cccc3c2c1] | US20090167162 |
| | 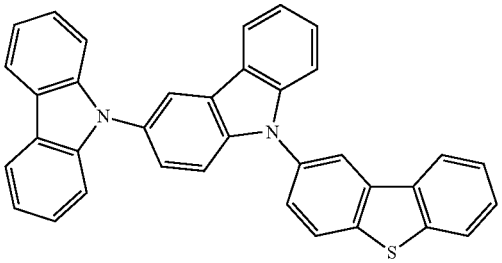 [SMILES: c1ccc2c(c1)sc1ccc(-n3c4ccccc4c4cc(-n5c6ccccc6c6ccccc65)ccc43)cc12] | WO2009086028 |
| | 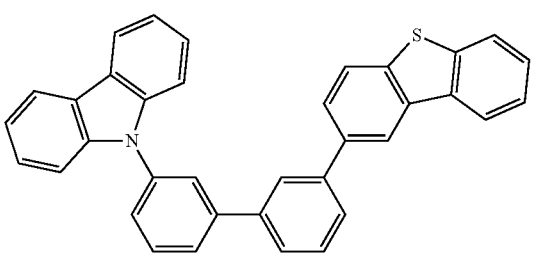 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 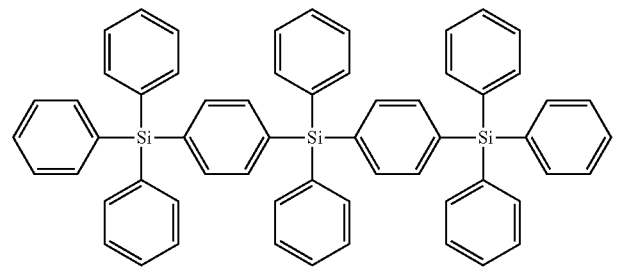 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 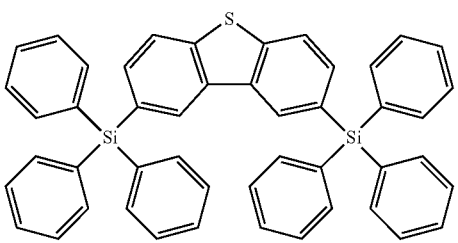 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATION |
| --- | --- | --- |
| Silicon/ Germanium aryl compounds | | EP2034538A |
| Aryl benzoyl ester | | WO2006100298 |
| High triplet metal organometallic complex | | US7154114 |

Phosphorescent dopants
Red dopants

| Heavy metal porphyrins (e.g., PtOEP) | | Nature 395, 151 (1998) |
| --- | --- | --- |
| Iridium (III) organometallic complexes | | Appl. Phys. Lett. 78, 1622 (2001) |

TABLE 2-continued

| MATERIAL | EXAMPLES OF MATERIAL | PUBLICATION |
|---|---|---|
| | | US2006835469 |
| | | US2006835469 |
| | | US20060202194 |
| | | US20060202194 |
| | | US20070087321 |

TABLE 2-continued

| MATERIAL | EXAMPLES OF MATERIAL | PUBLICATION |
| --- | --- | --- |
| | | US20070087321 |
| | | Adv. Mater. 19, 739 (2007) |
| | | WO2009100991 |
| | | WO2008101842 |
| Platinum (II) organometallic complexes | | WO2003040257 |

TABLE 2-continued

| MATERIAL | EXAMPLES OF MATERIAL | PUBLICATION |
|---|---|---|
| Osminum (III) complexes | [Os complex with CF$_3$-pyrazole-pyridine ligand, Os(PPhMe$_2$)$_2$] | Chem. Mater. 17, 3532 (2005) |
| Ruthenium (II) complexes | [Ru complex with tBu-pyrazole-isoquinoline ligand, Ru(PPhMe$_2$)$_2$] | Adv. Mater. 17, 1059 (2005) |
| Rhenium (I), (II), and (III) complexes | [Re(CO)$_4$ complex with 8-hydroxyquinoline ligand] | US20050244673 |

Green dopants

| MATERIAL | EXAMPLES OF MATERIAL | PUBLICATION |
|---|---|---|
| Iridium (III) organometallic complexes | [Ir(ppy)$_3$ complex] and its derivatives | Inorg. Chem. 40, 1704 (2001) |
| | [Ir(ppy)$_2$(acac) complex] | US20020034656 |

TABLE 2-continued

| MATERIAL | EXAMPLES OF MATERIAL | PUBLICATION |
|---|---|---|
| | | US7332232 |
| | | US20090108737 |
| | | US20090039776 |
| | | US6921915 |

TABLE 2-continued

| MATERIAL | EXAMPLES OF MATERIAL | PUBLICATION |
|---|---|---|
| | | US6687266 |
| | | Chem. Mater. 16, 2480 (2004) |
| | | US20070190359 |
| | | US 20060008670<br>JP2007123392 |
| | | Adv. Mater. 16, 2003 (2004) |

TABLE 2-continued

| MATERIAL | EXAMPLES OF MATERIAL | PUBLICATION |
|---|---|---|
| | | Angew. Chem. Int. Ed. 2006, 45, 7800 |
| | | WO2009050290 |
| | | US20090165846 |
| | | US20080015355 |
| Monomer for polymeric metal organometallic compounds | | US7250226, US7396598 |

TABLE 2-continued
| MATERIAL | EXAMPLES OF MATERIAL | PUBLICATION |
|---|---|---|
| Pt(II) organometallic complexes, including polydentated ligands | 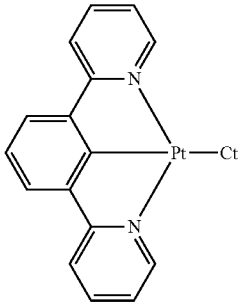 | Appl. Phys. Lett. 86, 153505 (2005) |
| | 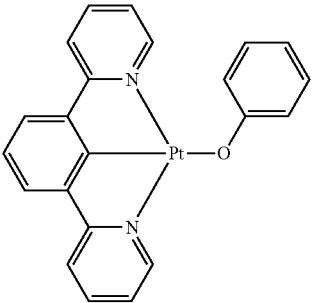 | Appl. Phys. Lett. 86, 153505 (2005) |
| | 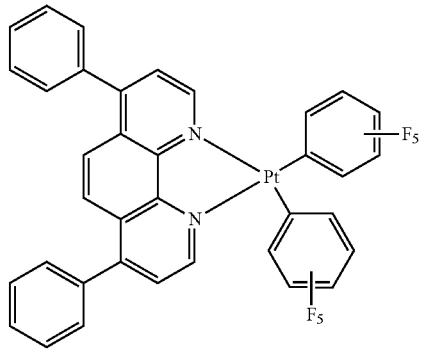 | Chem. Lett. 34, 592 (2005) |
| | 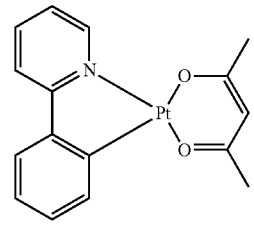 | WO2002015645 |
| | 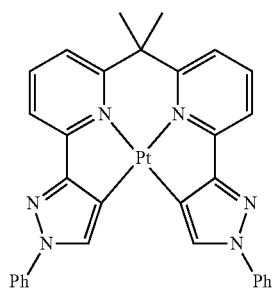 | US20060263635 |

TABLE 2-continued
| MATERIAL | EXAMPLES OF MATERIAL | PUBLICATION |
|---|---|---|
| Cu complexes | 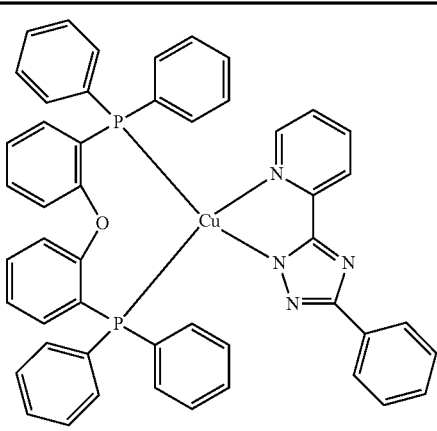 | WO2009000673 |
| Gold complexes | 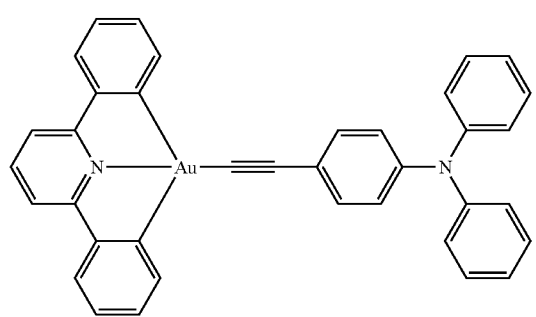 | Chem. Commun. 2906 (2005) |
| Rhenium (III) complexes | 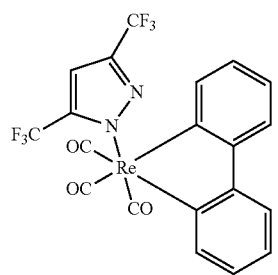 | Inorg. Chem. 42, 1248 (2003) |
| Deuterated organometallic complexes | 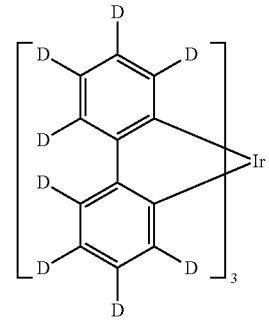 | US20030138657 |

TABLE 2-continued

| MATERIAL | EXAMPLES OF MATERIAL | PUBLICATION |
|---|---|---|
| Organometallic complexes with two or more metal centers | | US20030152802 |
| | | US7090928 |
| Blue dopants | | |
| Iridium (III) organometallic complexes | | WO2002002714 |
| | | WO2006009024 |
| | | US20060251923 |

TABLE 2-continued

| MATERIAL | EXAMPLES OF MATERIAL | PUBLICATION |
|---|---|---|
| | | US7393599, WO2006056418, US20050260441, WO2005019373 |
| | | US7534505 |
| | | US7445855 |
| | | US20070190359, US20080297033 |
| | | US7338722 |
| | | US20020134984 |

TABLE 2-continued
| MATERIAL | EXAMPLES OF MATERIAL | PUBLICATION |
|---|---|---|
| | 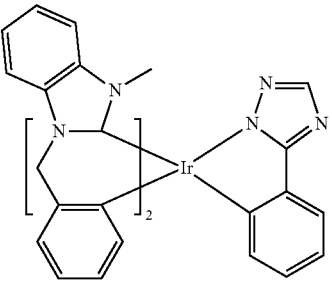 | Angew. Chem. Int. Ed. 47, 1 (2008) |
| | 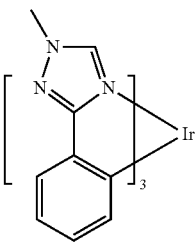 | Chem. Mater. 18, 5119 (2006) |
| | 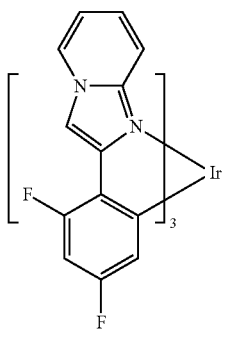 | Inorg. Chem. 46, 4308 (2007) |
| | 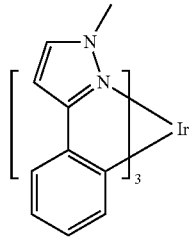 | WO2005123873 |
| | 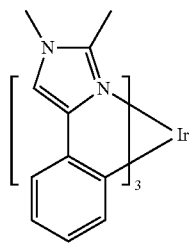 | WO2005123873 |
| | 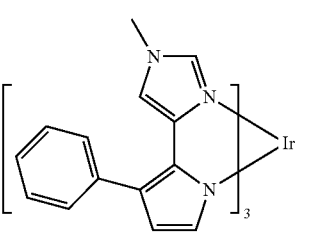 | WO2007004380 |

TABLE 2-continued

| MATERIAL | EXAMPLES OF MATERIAL | PUBLICATION |
|---|---|---|
|  |  | WO2006082742 |
| Osmium (II) complexes |  | US7279704 |
|  |  | Organometallics 23, 3745 (2004) |
| Gold complexes |  | Appl. Phys. Lett. 74, 1361 (1999) |

TABLE 2-continued

| MATERIAL | EXAMPLES OF MATERIAL | PUBLICATION |
|---|---|---|
| Platinum (II) complexes | | WO2006098120, WO2006103874 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett 81, 162 (2002) |
| 5-member ring electron deficient heterocycles such as triazole, oxadiazole, imidazole, benzoimidazole | | Appl. Phys. Lett 81, 162 (2002) |

/ TABLE 2-continued
| MATERIAL | EXAMPLES OF MATERIAL | PUBLICATION |
|---|---|---|
| Triphenylene compounds | 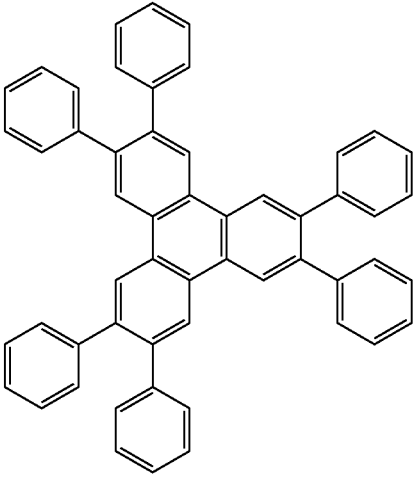 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 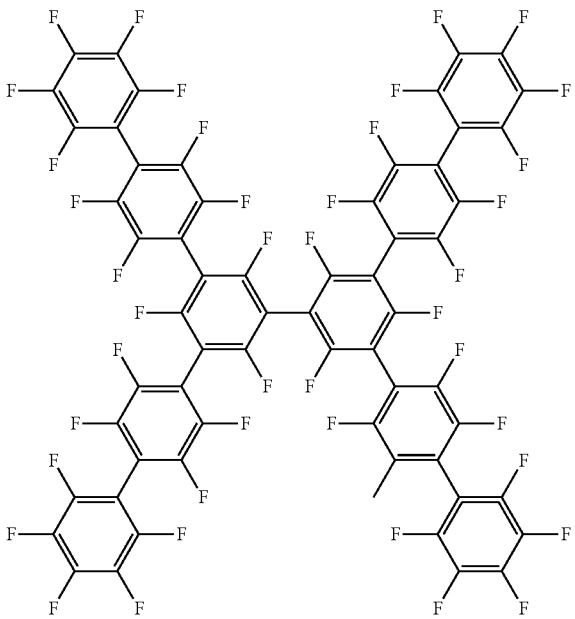 | Appl. Phys. Lett. 79, 156 (2001) |

TABLE 2-continued
| MATERIAL | EXAMPLES OF MATERIAL | PUBLICATION |
|---|---|---|
| Phenothiazine-S-oxide | 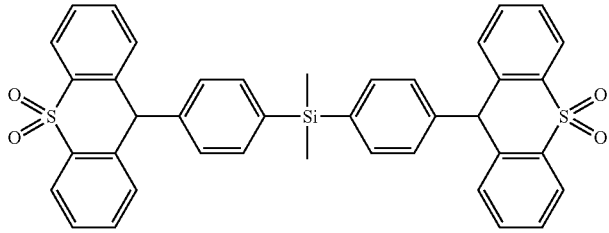 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Electron transporting materials | | |
| Anthracene-benzoimidazole compounds | 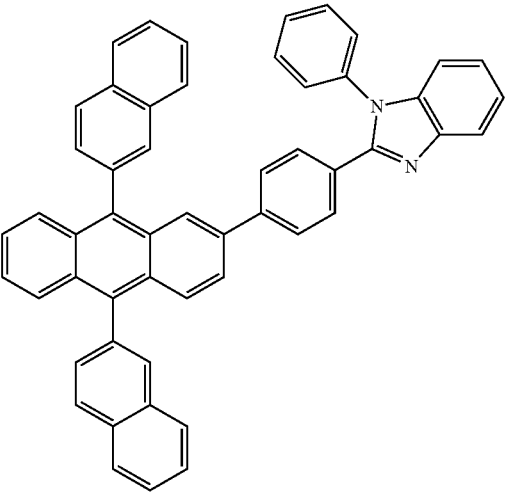 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
|  | 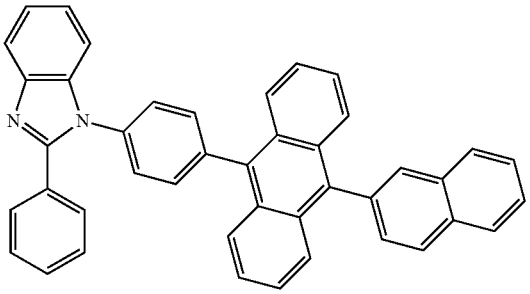 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 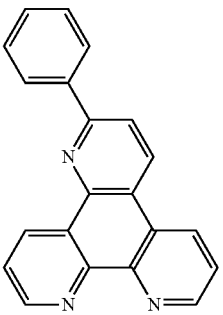 [SMILES: c1ccc(-c2ccc3c4cccnc4c4ncccc4c3n2)cc1] | US20090115316 |

TABLE 2-continued

| MATERIAL | EXAMPLES OF MATERIAL | PUBLICATION |
| --- | --- | --- |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) US7230107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g.,triazole, oxadiazole, imidazole, benzoimidazole) | | Appl. Phys. Lett. 74, 865 (1999) |

TABLE 2-continued
| MATERIAL | EXAMPLES OF MATERIAL | PUBLICATION |
|---|---|---|
| | 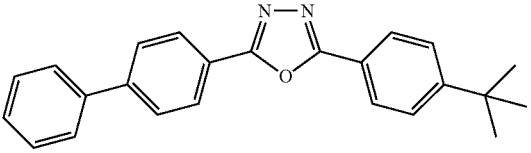 [SMILES: CC(C)(C)c1ccc(-c2nnc(-c3ccc(-c4ccccc4)cc3)o2)cc1] | Appl. Phys. Lett. 55, 1489 (1989) |
| | 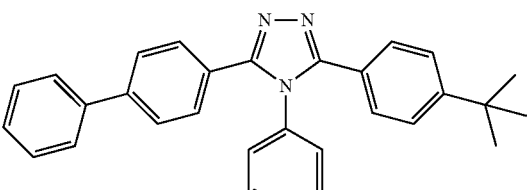 | Jpn. J. Apply. Phys. 32, L917 (1993) |
| Silole compounds | 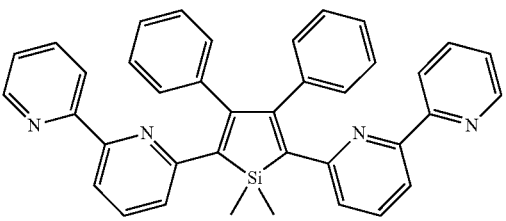 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 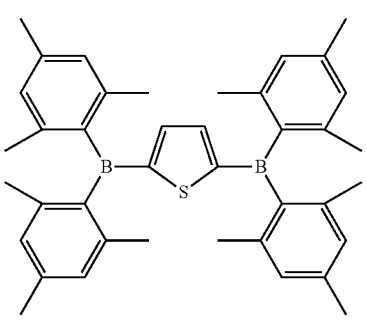 | J. Am. Chem. Soc. 120, 9714 (1998) |
| Fluorinated aromatic compounds | 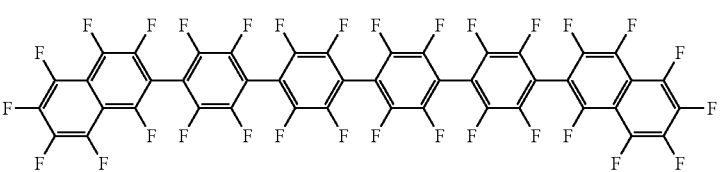 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 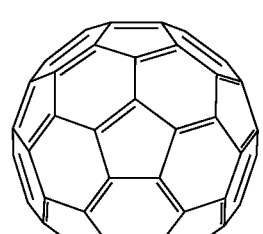 | US20090101870 |

TABLE 2-continued

| MATERIAL | EXAMPLES OF MATERIAL | PUBLICATION |
|---|---|---|
| Triazine complexes | | US20040036077 |
| Zn (N^N) complexes | 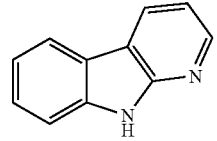 | US6528187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

EXAMPLES

Chemical abbreviations used throughout this document are as follows: PPh$_3$ is triphenylphosphine, DCM is dichloromethane, dba is dibenzylideneacetone, Cy is cyclohexyl, OAc is acetate, DBU is 1,8-diazabicyclo[5.4.0]undec-7-ene, dppf is 1,1'-bis(diphenylphosphino)ferrocene, THF is tetrahydrofuran.

Synthesis of Compound 1

Step 1

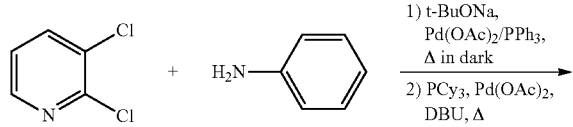

-continued

Into a mixture of sodium tert-butoxide (11.69 g, 122 mmol), triphenylphosphine (2.66 g, 10.14 mmol), palladium acetate (1.138 g, 5.07 mmol), 2,3-dichloropyridine (15 g, 101 mmol) and aniline (10.18 ml, 111 mmol) was added o-xylene (100 mL). The solution was degased by vacuum-nitrogen cycles before heating at 120° C. in the absence of light for 3 hours and cooled to room temperature. In another flask, tri-cyclohexylphosphine (16.04 ml, 10.14 mmol), palladium acetate (1.138 g, 5.07 mmol), and DBU (30.6 ml, 203 mmol) were dissolved in dimethylacetamide (100 ml). This solution was degassed by vacuum/nitrogen cycles and transferred to the above reaction mixture. The resultant reaction mixture was stirred at 150° C. for another 12 hours, cooled to room temperature and quenched with water. The aqueous phase was extracted with ethyl acetate. The combined organic phase was washed with aqueous LiCl (10 wt %) solution, dried over MgSO$_4$. Upon evaporation off the solvent, the black residue was precipitated from dichloromethane into hexane. The crude product was purified by recrystallization from toluene to yield 9H-pyrido[2,3-b]indole as a yellowish white product (9.0 g).

Step 2

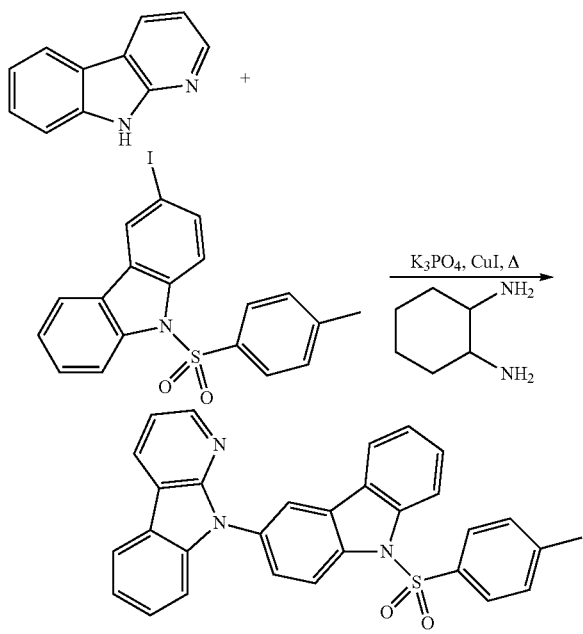

The synthesis of N-tosyl-3-iodocarbazole is described in WO2009/086028. Into a 250 mL flask was added 9H-pyrido[2,3-b]indole (5 g, 29.7 mmol), N-tosyl-3-iodocarbazole (14.63 g, 32.7 mmol), copper(I) iodide (0.283 g, 1.486 mmol) and potassium phosphate (13.25 g, 62.4 mmol). It was degassed before the addition of anhydrous m-xylene (150 mL) and cyclohexane-1,2-diamine (0.339 g, 2.97 mmol). The resultant green suspension was refluxed for three days. Column chromatography on silica gel (eluent hexane/DCM 1:4, v/v) provided the product 9-(9-tosyl-carbazol-3-yl)-pyrido[2,3-b]indole (9.9 g).

Step 3

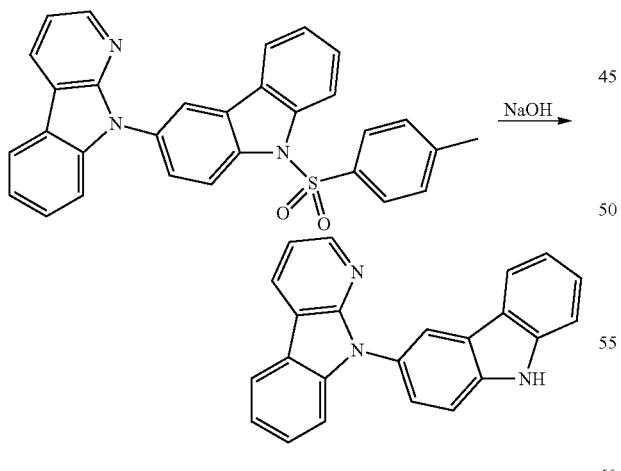

A mixture solution of 9-(9-tosyl-carbazol-3-yl)-pyrido[2,3-b]indole (9.9 g, 20.30 mmol) and NaOH (8.12 g, 203 mmol) in THF (100 mL), ethanol (50 mL) and water (50 mL) was refluxed over weekend. After cooling to room temperature, the white solid was obtained by filtration, and washed successively with water, ethanol, DCM and ethanol to yield the 9-(9H-carbazol-3-yl)-9H-pyrido[2,3-b]indole (4.8 g).

Synthesis of 4-(3'-bromo-[1',1'-biphenyl]-3-yl)dibenzo[b,d]thiophene

1. Synthesis of 4-(3-bromophenyl)dibenzo[b,d]thiophene

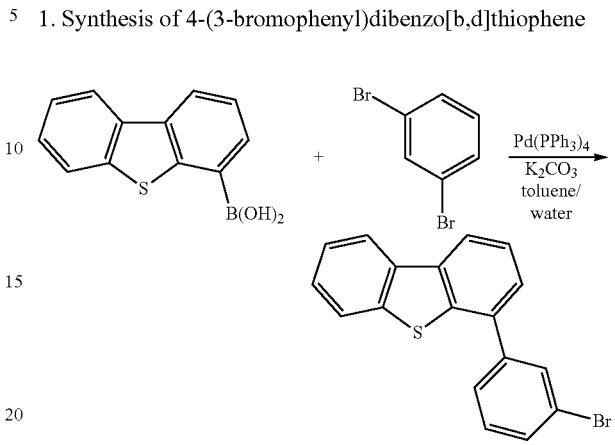

Dibenzo[b,d]thiophen-4-yl-boronic acid (10.00 g, 43.8 mmol), 1,3-dibromobenzene (20.69 g, 88 mmol) and $Pd(PPh_3)_4$ catalyst (0.507 g, 0.438 mmol) were dissolved in 200 mL of toluene, and potassium carbonate (18.18 g, 132 mmol) in 50 mL of water was added, and the mixture was refluxed overnight under $N_2$. The mixture was cooled to room temperature, and the organic layer was separated, filtered and evaporated. The residue after evaporation was purified by column chromatography on silica gel (eluted with hexane/DCM 95/5 v/v mixture), followed by recrystallization from hexane. 4-(3-bromophenyl)dibenzo[b,d]thiophene was obtained as white solid (12 g, 81% yield).

2. Synthesis of 2-(3-(dibenzo[b,d]thiophen-4-yl)phenyl)-4,4,5,5-tetramethyl-1,3,2-dioxaborolane

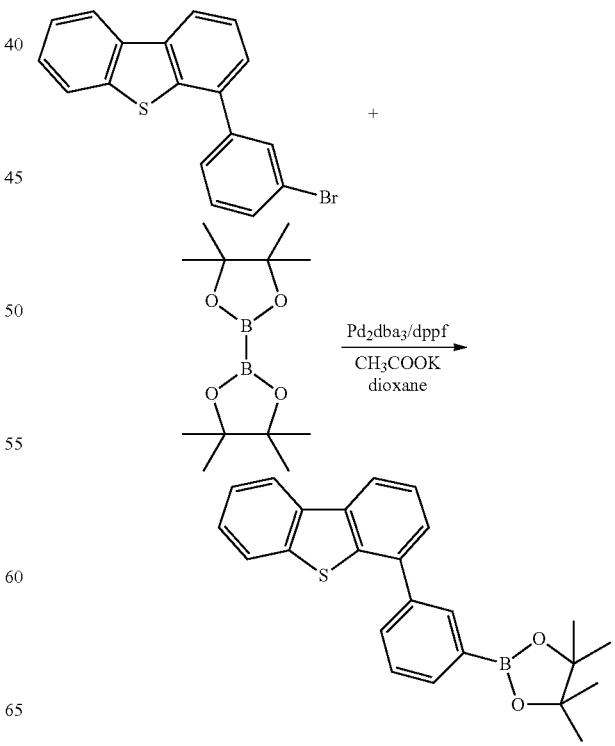

4-(3-bromophenyl)dibenzo[b,d]thiophene (18.50 g, 54.5 mmol) and 4,4,4',4',5,5,5',5'-octamethyl-2,2'-bi(1,3,2-dioxaborolane) (18.00 g, 70.9 mmol) were dissolved in 200 mL of dioxane, and to the dioxane solution potassium acetate (10.70 g, 109 mmol), 1,1'-bis(diphenylphosphino) ferrocene (0.666 g, 1.091 mmol) and tris(dibenzylideneacetone)dipalladium (0) (0.499 g, 0.545 mmol) were added. The reaction mixture was degassed and heated to reflux overnight, cooled down to room temperature, filtered and evaporated. Column chromatography on silica gel with hexane/DCM 95/5 v/v eluent provided 2-(3-(dibenzo[b,d]thiophen-4-yl)phenyl)-4,4,5,5-tetramethyl-1,3,2-dioxaborolane as white solid (15.1 g, 71%).

3. Synthesis of 4-(3'-bromo-[1,1'-biphenyl]-3-yl)dibenzo[b,d]thiophene

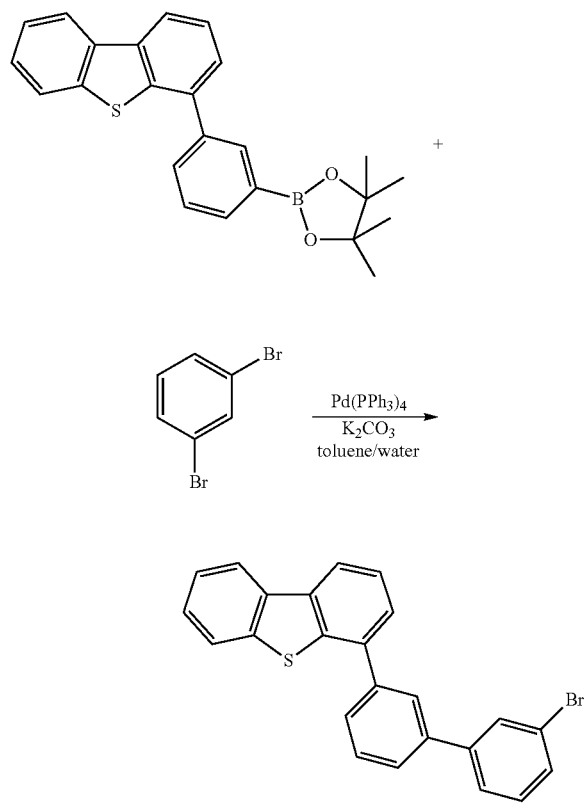

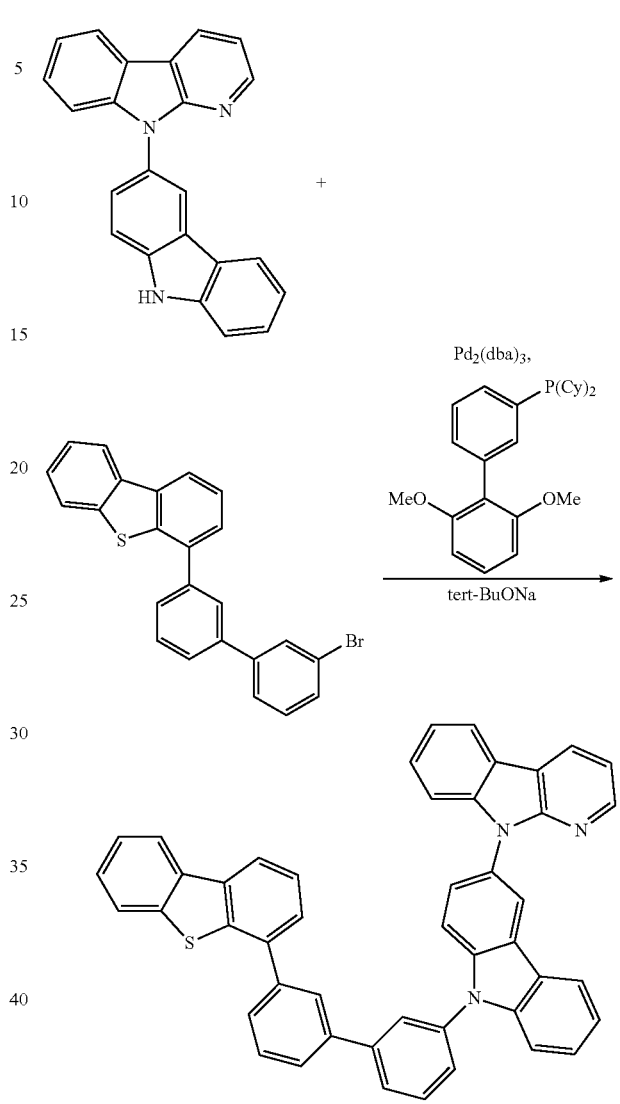

2-(3-(dibenzo[b,d]thiophen-4-yl)phenyl)-4,4,5,5-tetramethyl-1,3,2-dioxaborolane (8.80 g, 22.78 mmol) and 1,3-dibromobenzene (21.49 g, 91 mmol) were dissolved in toluene (300 mL), and potassium carbonate (9.44 g, 68.3 mmol) in 50 mL of water and the Pd(PPh$_3$)$_4$ catalyst (0.263 g, 0.228 mmol) were then added. The reaction mixture was degassed and refluxed under N$_2$ overnight. The organic layer was then separated, evaporated and subjected to column chromatography on silica gel, eluted with hexane/DCM 9:1 v/v mixture, providing 4-(3'-bromo-[1,1'-biphenyl]-3-yl)dibenzo[b,d]thiophene (7.5 g, 18.06 mmol, 79% yield) as white solid.

Step 4

A solution of 9-(9H-carbazol-3-yl)-pyrido[2,3-b]indole (2.50 g, 7.50 mmol), 4-(3'-bromo-[1,1'-biphenyl]-3-yl) dibenzo[b,d]thiophene (3.11 g, 7.50 mmol), Pd$_2$(dba)$_3$ (0.137 g, 0.150 mmol), dicyclohexyl(2',6'-dimethoxy-[1,1'-biphenyl]-3-yl)phosphine (0.123 g, 0.30 mmol), and sodium tert-butoxide (1.44 g, 15.00 mmol) in xylene (150 mL) was refluxed in nitrogen overnight. After cooling to room temperature, the reaction mixture was washed with water, dried over Na$_2$SO$_4$ and the solvent was evaporated. The residue was dissolved in hot toluene, mixed with celite, and purified by column chromatography with hexane:toluene (1:9 to 0:10, v/v) as eluent. The product was precipitated in ethanol, and further purified by thermal sublimation under vacuum (<10$^5$ torr) to yield 9-(9-(3'-(dibenzo[b,d]thiophen-4-yl)-[1,1'-biphenyl]-3-yl)-carbazol-3-yl)-pyrido[2,3-b]indole as a white glassy solid (3.21 g).

The invention claimed is:
1. A compound of formula I:

Y—X—Z,   Formula I, wherein Y is selected from the group consisting of:

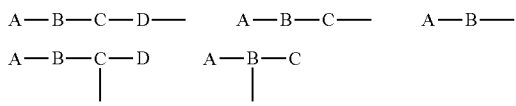

wherein A, B, C, and D are independently selected from the compound of formula II:

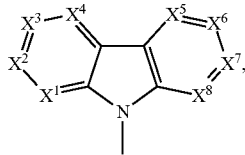

Formula II wherein
X¹ is selected from the group C—R¹ and N;
X² is selected from the group C—R² and N;
X³ is selected from the group C—R³ and N;
X⁴ is selected from the group C—R⁴ and N;
X⁵ is selected from the group C—R⁵ and N;
X⁶ is selected from the group C—R⁶ and N;
X⁷ is selected from the group C—R⁷ and N;
X⁸ is selected from the group C—R⁸ and N;
wherein A, B, C, and D are connected to each other through C—N bonds, where N is in the 9-position;
wherein at least one of A, B, C, and D is not carbazole;
wherein X is an aryl or heteroaryl linker that is optionally further substituted;
wherein Y and X are connected through a C—N bond, where the C—N bond is defined as a bond between a nitrogen atom at the 9-position in one of A, B, C, and D, if present, and a carbon atom of X;
wherein $R_1$, $R_2$, $R_3$, $R_4$, $R_5$, $R_6$, $R_7$, and $R_8$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein Z is selected from the group consisting of dibenzothiophene, dibenzofuran, dibenzoselenophene, aza-dibenzothiophene, aza-dibenzofuran, and aza-dibenzoselenophene that is optionally further substituted.

2. The compound of claim 1, wherein X is

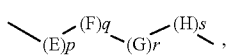

wherein E, F, G and H are independently selected from the group consisting of:

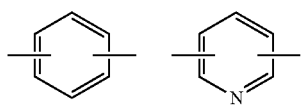

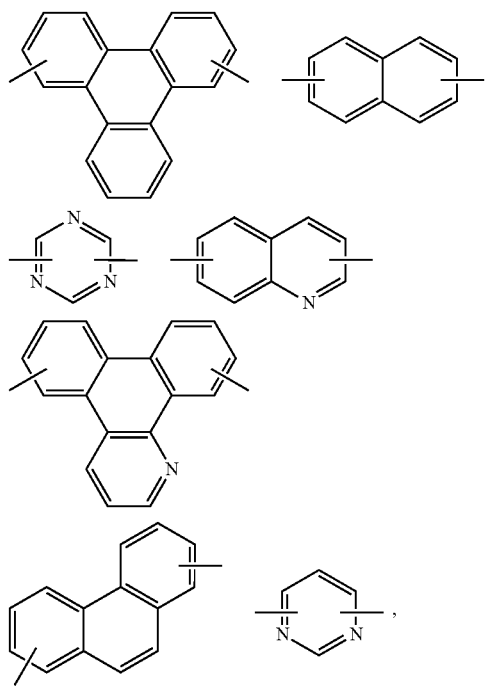

wherein E, F, G and H are optionally further substituted with $R_9$;

wherein $R_9$ represents mono, di, tri, or tetra substitutions;

wherein $R_9$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein each of p, q, r and s are 0, 1, 2, 3, or 4; and wherein p+q+r+s is at least 1.

3. The compound of claim 1, wherein A, B, C, and D are connected to each other through a bond between a carbon at the 3 or 6-position and a nitrogen at the 9-position.

4. The compound of claim 1, wherein Z is 2-dibenzothiophenyl, 4-dibenzothiophenyl, 2-dibenzofuranyl, or 4-dibenzofuranyl.

5. The compound of claim 1, wherein A, B, C, and D are not carbazole.

6. The compound of claim 1, wherein $R_1$, $R_2$, $R_3$, $R_4$, $R_5$, $R_6$, $R_7$, and $R_8$, if present, are independently selected from the group consisting of phenyl, biphenyl, triphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, azaindole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine and thienodipyridine.

7. The compound of claim 1, wherein A, B, C, and D are independently selected from the group consisting of:
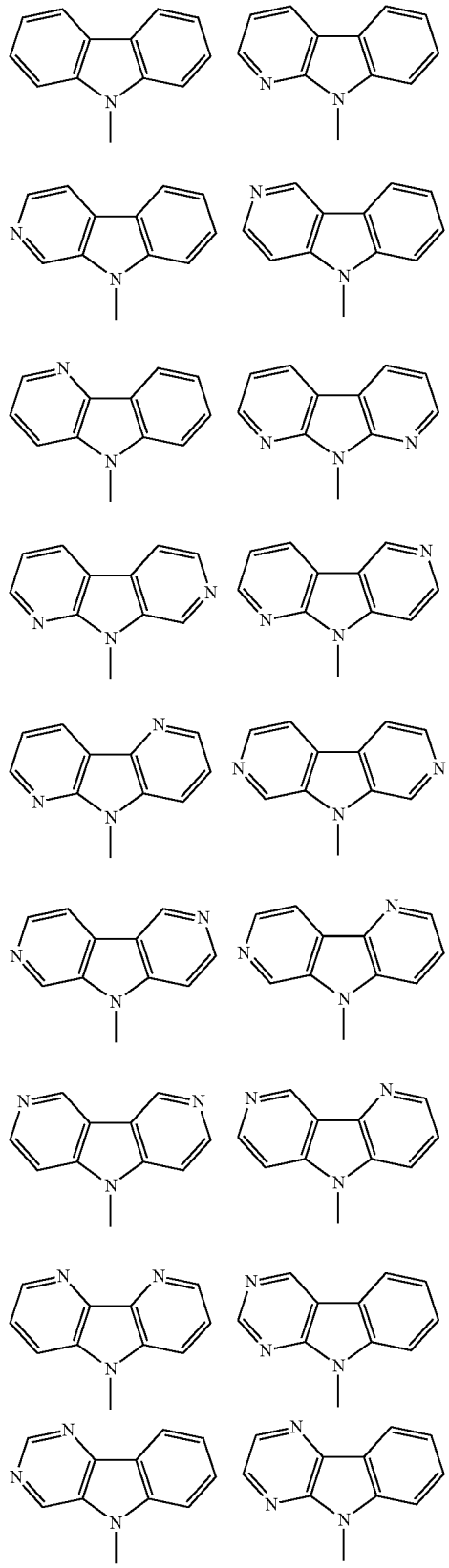
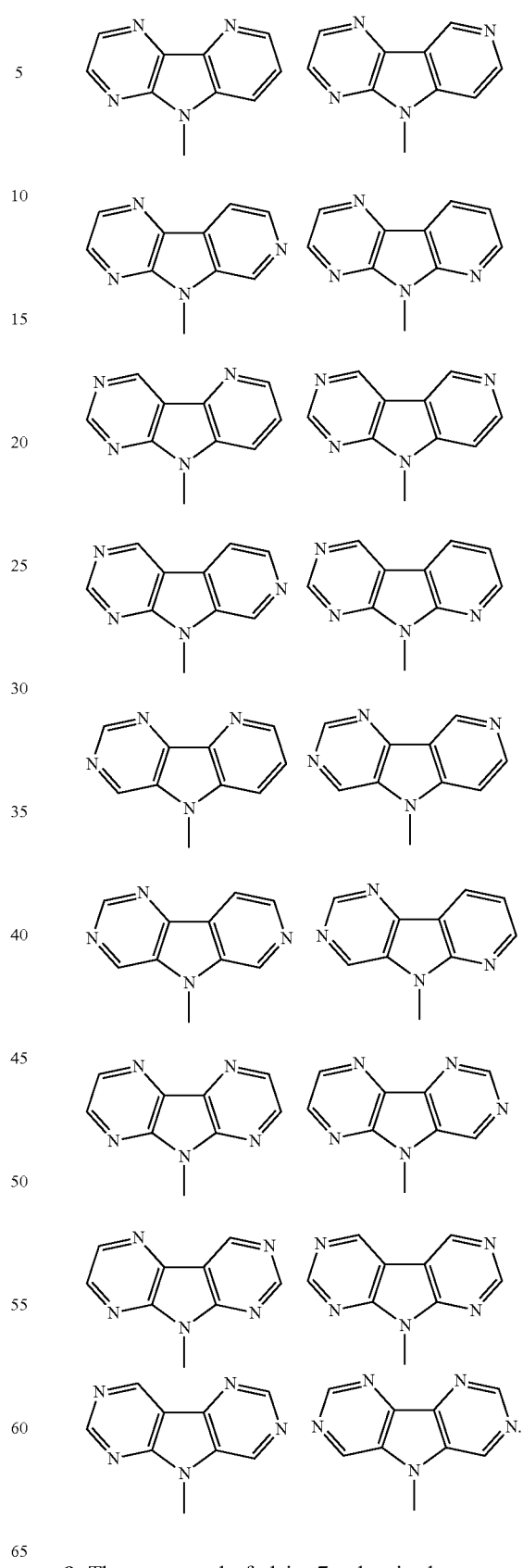
8. The compound of claim 7, wherein the compound is selected from the group consisting of:

Compound 1
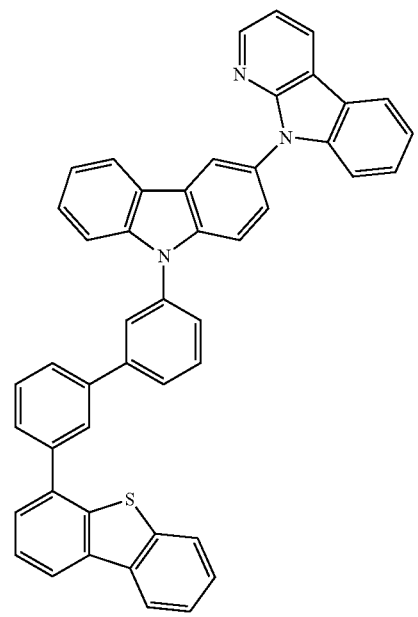
Compound 2
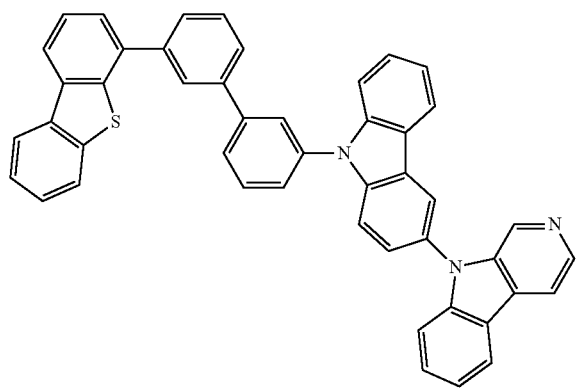
Compound 3
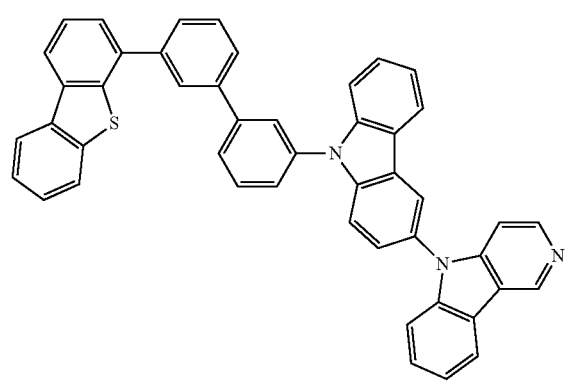
Compound 4
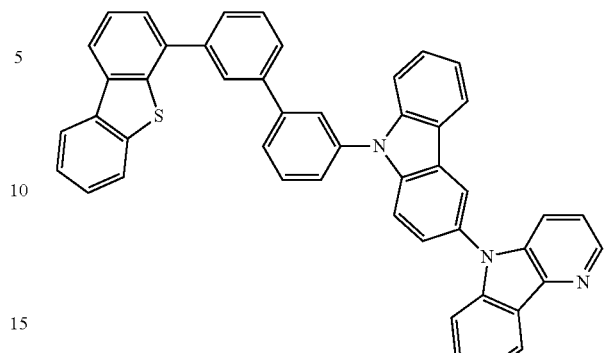
Compound 5
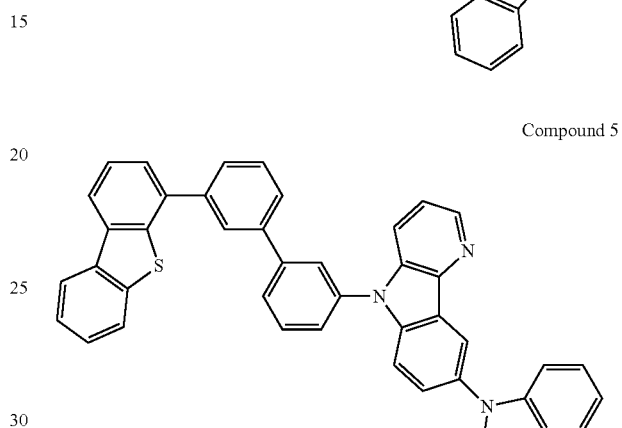
Compound 6
Compound 7
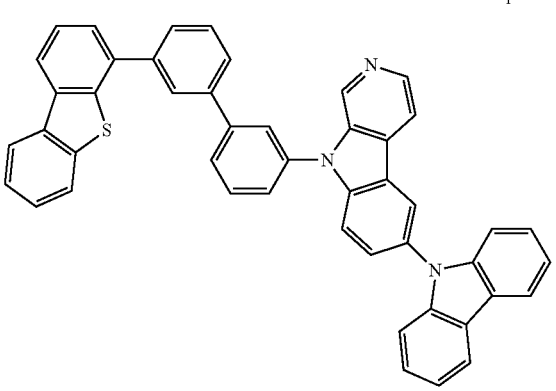

Compound 8
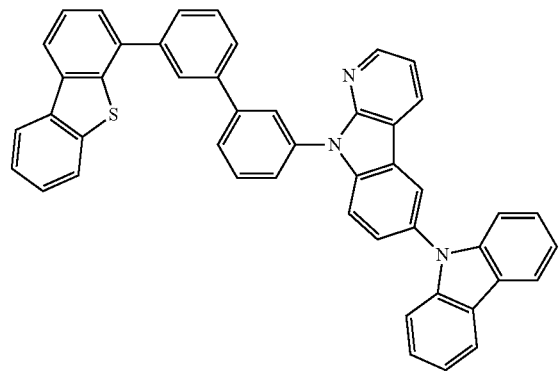
Compound 9
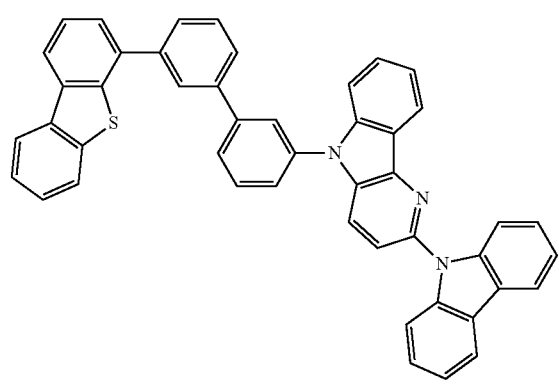
Compound 10
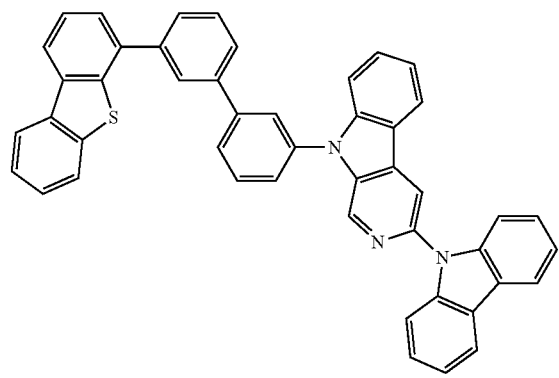
Compound 11
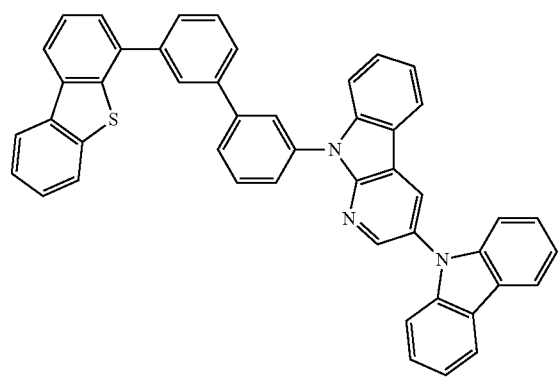
Compound 12
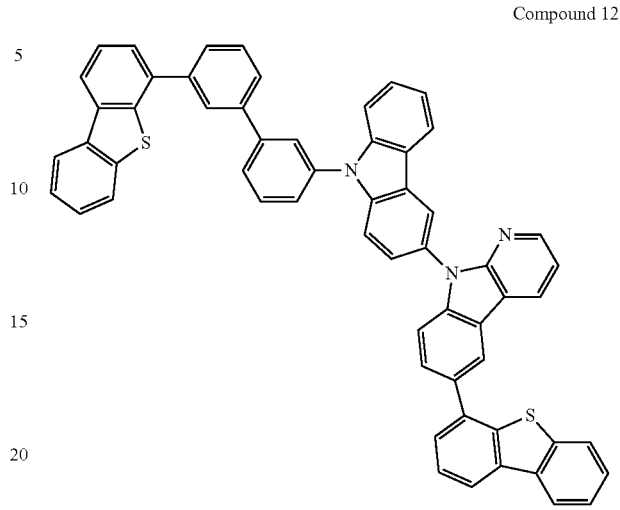
Compound 13
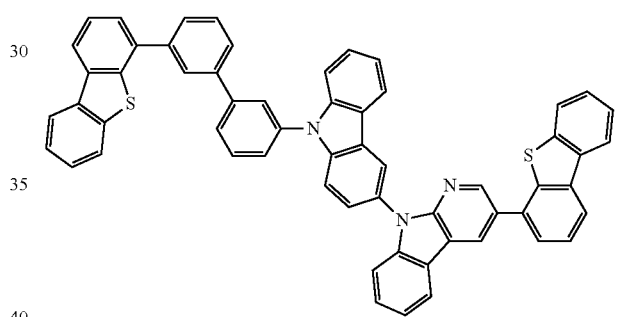
Compound 14
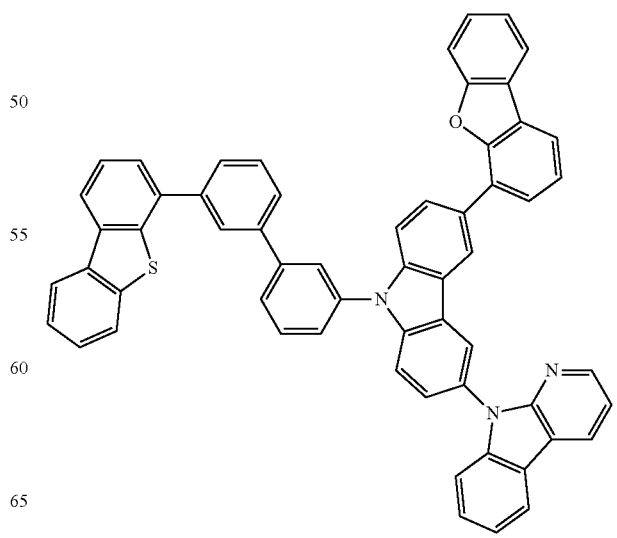

Compound 15
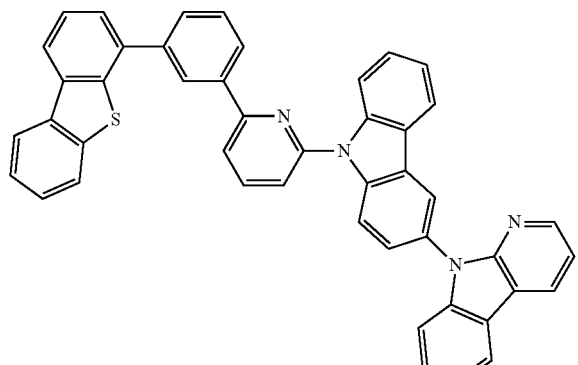
Compound 16
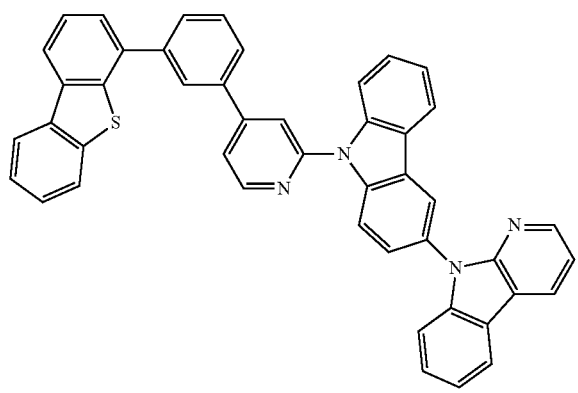
Compound 17
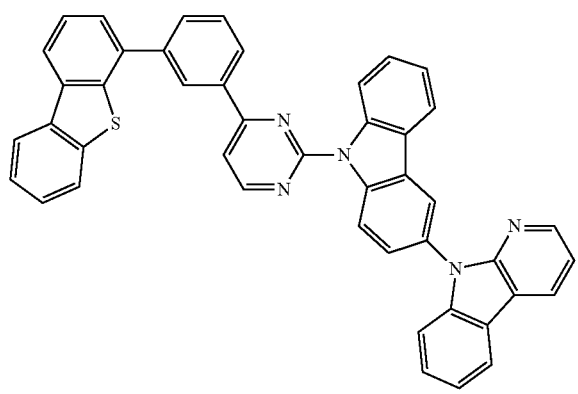
Compound 18
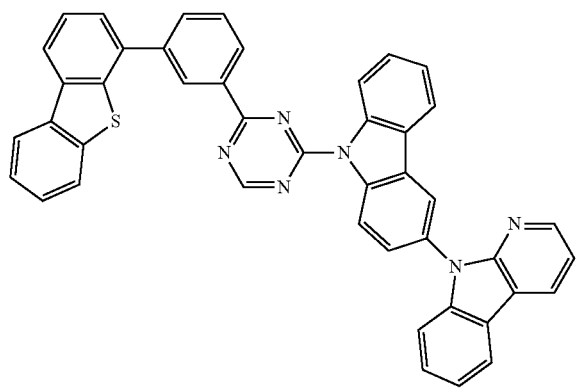
Compound 19
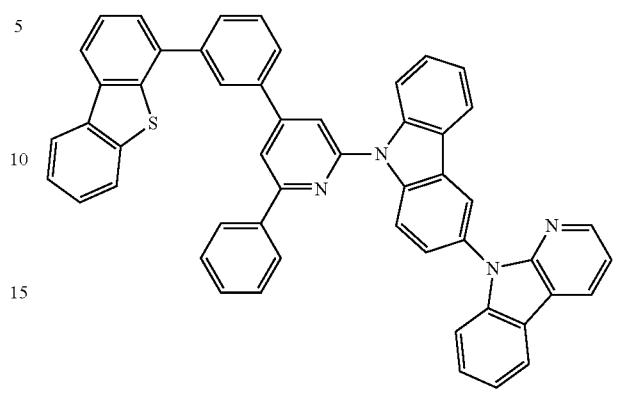
Compound 20
Compound 21
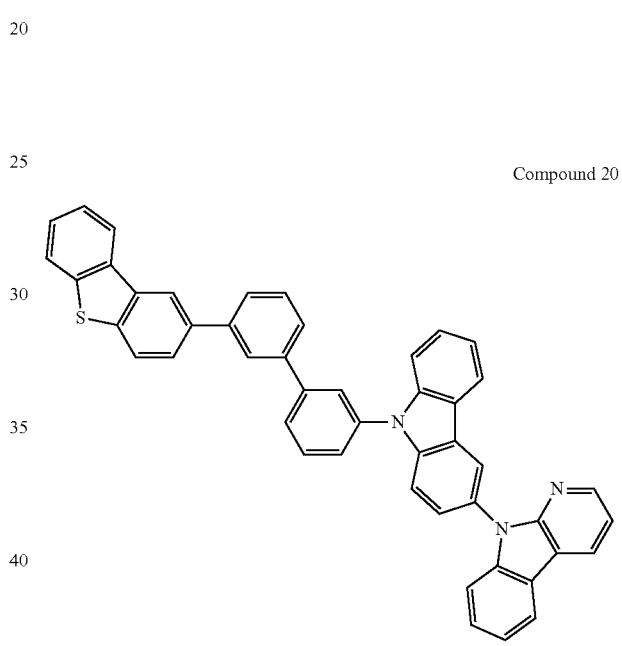

Compound 22
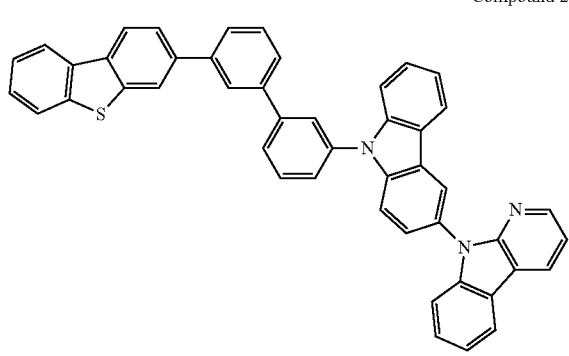
Compound 23
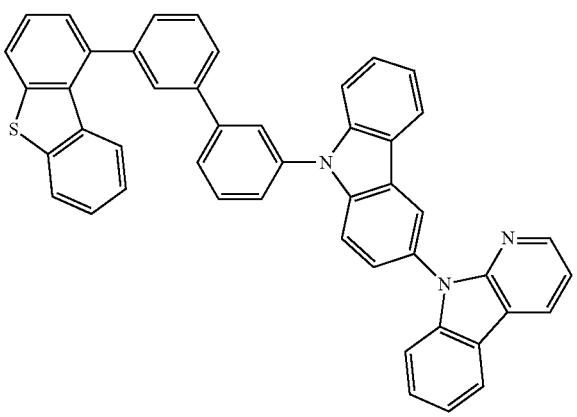
Compound 24
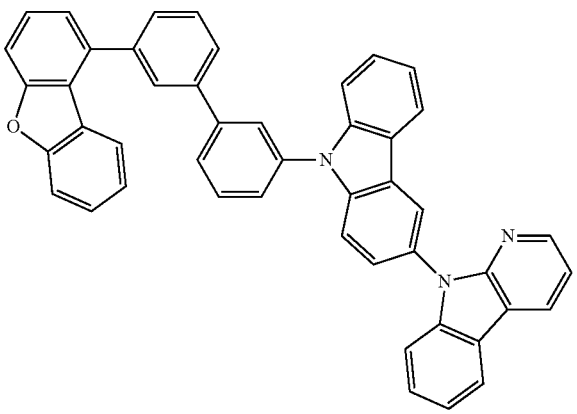
Compound 25
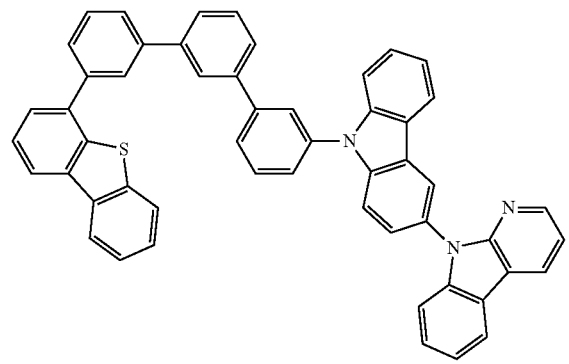
Compound 26
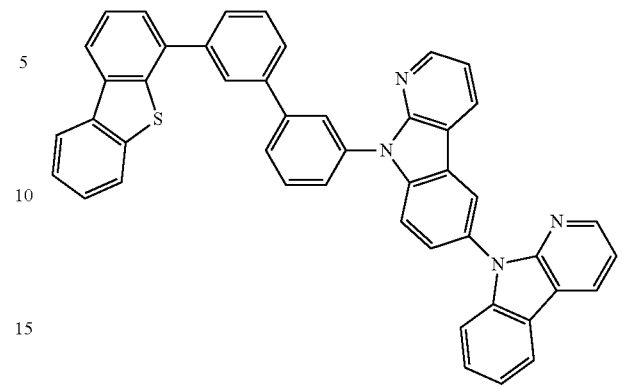
Compound 27
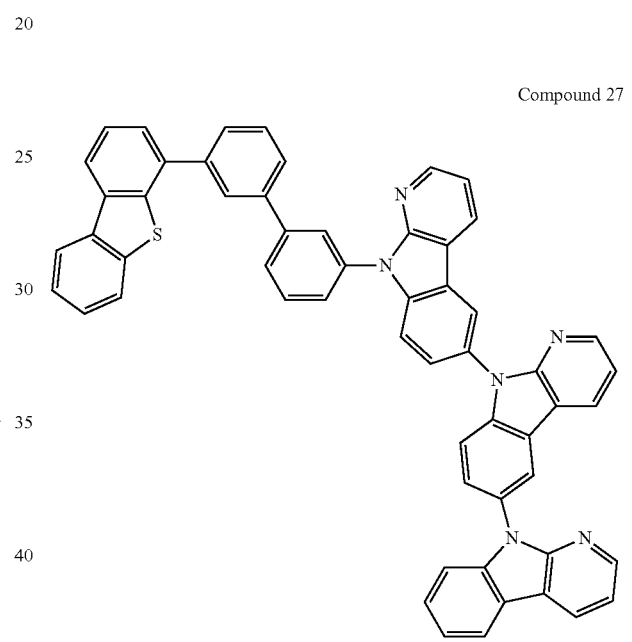
Compound 28
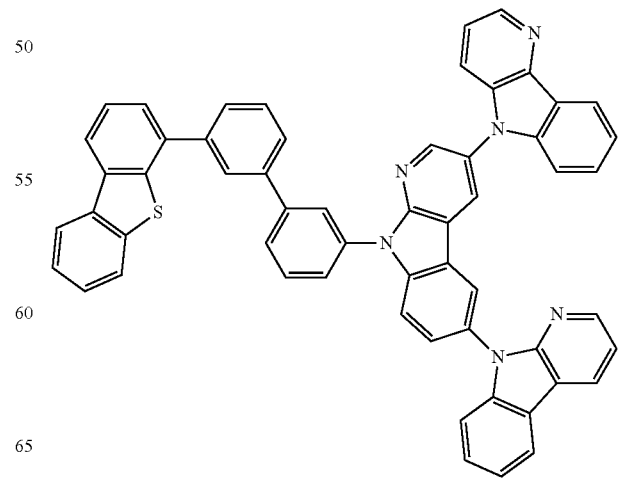

Compound 29
Compound 30
Compound 31
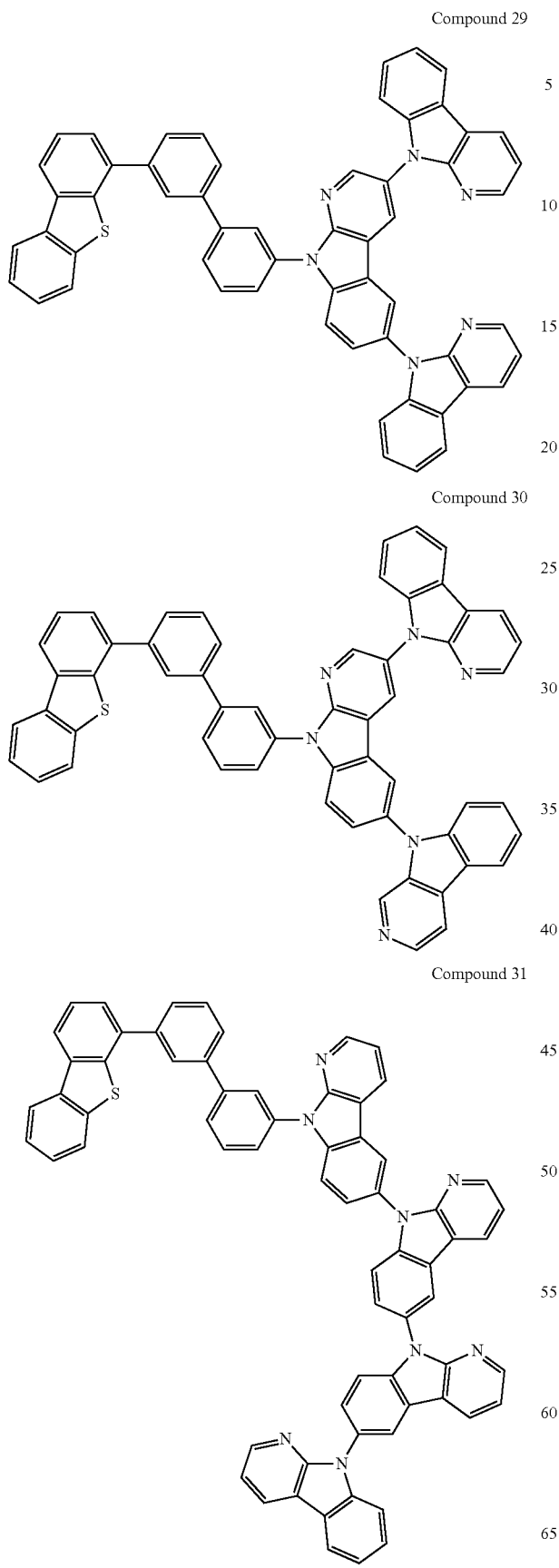
Compound 32
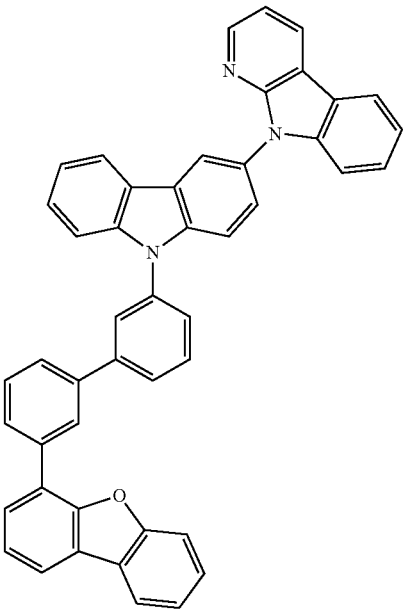
Compound 33
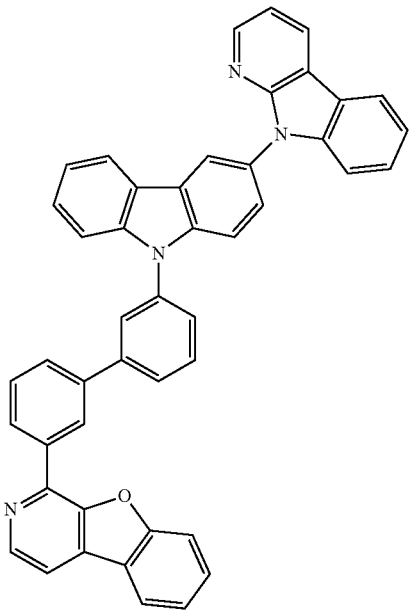
Compound 34
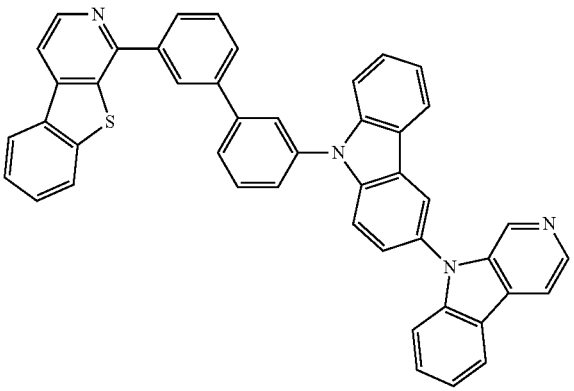

Compound 35

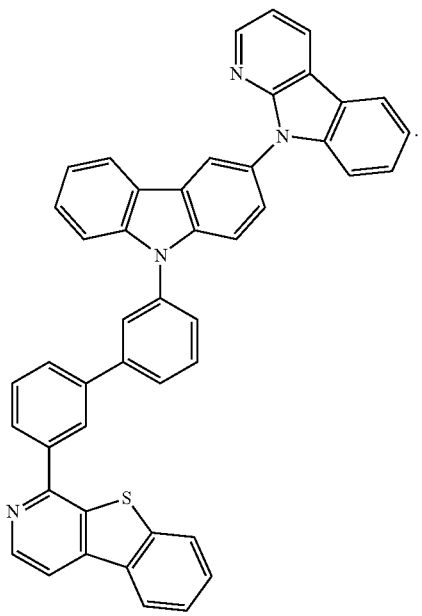

9. A first device, comprising an organic light emitting device comprising:
an anode;
a cathode; and
a first organic layer disposed between the anode and the cathode, comprising a compound having the formula I:

Y—X—Z   Formula I, wherein Y is selected from the group consisting of:

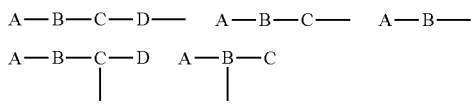

wherein A, B, C, and D are independently selected from the compound of formula II:

Formula II

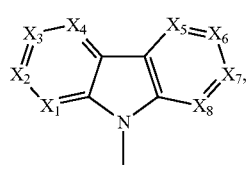

wherein
$X^1$ is selected from the group C—$R^1$ and N;
$X^2$ is selected from the group C—$R^2$ and N;
$X^3$ is selected from the group C—$R^3$ and N;
$X^4$ is selected from the group C—$R^4$ and N;
$X^5$ is selected from the group C—$R^5$ and N;
$X^6$ is selected from the group C—$R^6$ and N;
$X^7$ is selected from the group C—$R^7$ and N;
$X^8$ is selected from the group C—$R^8$ and N;
wherein A, B, C, and D are connected to each other through C—N bonds, where N is in the 9-position;
wherein at least one of A, B, C, and D is not carbazole;

wherein X is an aryl or heteroaryl linker that is optionally further substituted;

wherein Y and X are connected through a C—N bond, where the C—N bond is defined as a bond between a nitrogen atom at the 9-position in one of A, B, C, and D, if present, and a carbon atom of X;

wherein R', R'', $R_1$, $R_2$, $R_3$, $R_4$, $R_5$, $R_6$, $R_7$, and $R_8$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein Z is selected from the group consisting of dibenzothiophene, dibenzofuran, dibenzoselenophene, aza-dibenzothiophene, aza-dibenzofuran, and aza-dibenzoselenophene that is optionally further substituted.

10. The first device of claim 9, wherein the first organic layer is an emissive layer and the compound of formula I is a host.

11. The first device of claim 10, wherein the organic layer further comprises an emissive compound.

12. The first device of claim 11, wherein the emissive compound is a transition metal complex having at least one ligand selected from the group consisting of:

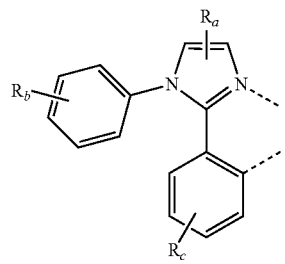

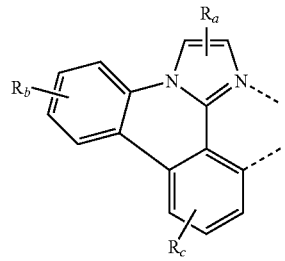

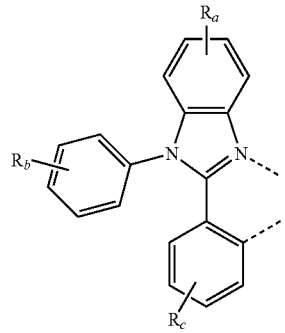

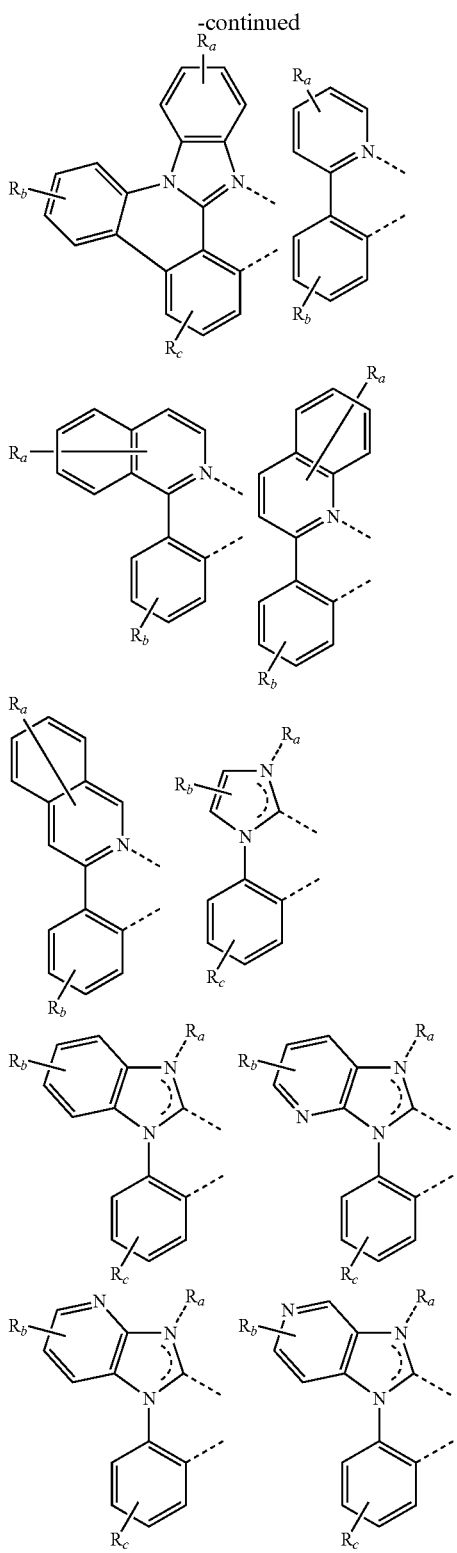
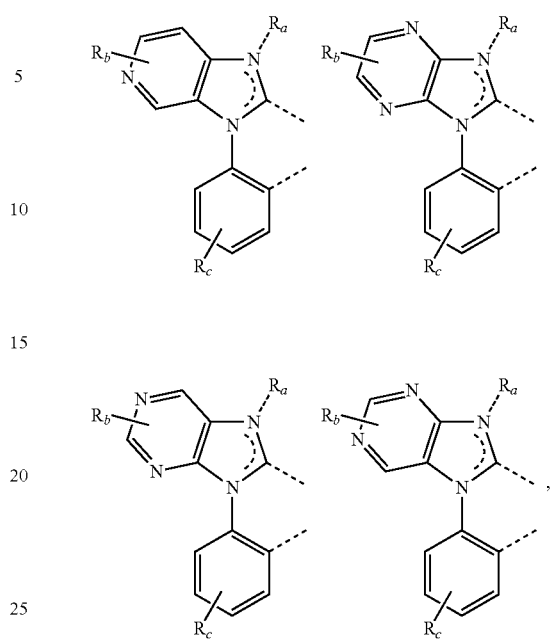

wherein $R_a$, $R_b$, and $R_c$ independently represent mono, di, tri or tetra substitutions;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and R, are optionally joined to form a fused ring.

13. The first device of claim 9, wherein the device further comprises a second organic layer that is a non-emissive layer and the compound having formula I is a material in the second organic layer.

14. The first device of claim 13, wherein the second organic layer is an electron transporting layer and the compound having the formula I is an electron transporting material in the second organic layer.

15. The first device of claim 13, wherein the second organic layer is a blocking layer and the compound having the formula I is a blocking material in the second organic layer.

16. The first device of claim 9, wherein the device is an organic light emitting device.

17. The first device of claim 9, wherein the device is a consumer product.

* * * * *